US010426728B2

(12) United States Patent
Ali et al.

(10) Patent No.: US 10,426,728 B2
(45) Date of Patent: Oct. 1, 2019

(54) SYNERGISTIC LIPOSOMAL FORMULATION FOR THE TREATMENT OF CANCER

(71) Applicant: Council of Scientific and Industrial Research, New Delhi (IN)

(72) Inventors: Nahid Ali, Jadavpur (IN); Manjarika De, Jadavpur (IN); Triparna Sen, Jadavpur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/023,107

(22) PCT Filed: Sep. 18, 2014

(86) PCT No.: PCT/IN2014/000610
§ 371 (c)(1),
(2) Date: Mar. 18, 2016

(87) PCT Pub. No.: WO2015/040636
PCT Pub. Date: Mar. 26, 2015

(65) Prior Publication Data
US 2016/0228366 A1 Aug. 11, 2016

(30) Foreign Application Priority Data

Sep. 19, 2013 (IN) .......................... 2756/DEL/2013

(51) Int. Cl.
| | |
|---|---|
| A61K 9/00 | (2006.01) |
| A61K 47/18 | (2017.01) |
| A61K 47/24 | (2006.01) |
| A61K 9/127 | (2006.01) |
| A61K 31/542 | (2006.01) |
| A61K 31/704 | (2006.01) |

(52) U.S. Cl.
CPC .......... *A61K 9/1272* (2013.01); *A61K 9/0019* (2013.01); *A61K 31/542* (2013.01); *A61K 31/704* (2013.01); *A61K 47/18* (2013.01); *A61K 47/24* (2013.01)

(58) Field of Classification Search
CPC .... A61K 31/542; A61K 31/704; A61K 47/18; A61K 47/24; A61K 9/0019; A61K 9/1272
See application file for complete search history.

(56) References Cited

U.S. PATENT DOCUMENTS

| | | | |
|---|---|---|---|
| 4,419,348 A | 12/1983 | Rahman et al. | |
| 2002/0142048 A1* | 10/2002 | Sands | A61K 9/1075 424/498 |
| 2013/0017248 A1 | 1/2013 | Graham et al. | |

FOREIGN PATENT DOCUMENTS

| | | |
|---|---|---|
| EP | 2311490 A2 | 4/2011 |
| WO | WO-2015/040636 | 3/2015 |
| WO | WO-2015/040636 A4 | 3/2015 |

OTHER PUBLICATIONS

"International Application No. PCT/IN2014/000610, Article 19 amendment dated Mar. 16, 2015", (Mar. 16, 2015), 8 pgs.
"International Application No. PCT/IN2014/000610, International Search Report and Written Opinion dated Jan. 16, 2015", (Jan. 16, 2015), 11 pgs.
Lin, Chih-Hung, et al., "Camptothecin-Loaded Liposomes with a-Melanocyte-Stimulating Hormone Enhance Cytotoxicity Toward and Cellular Uptake by Melanomas: An Application of Nanomedicine on Natural Product", J Tradit Complement Med. Apr.-Jun. 2013; 3(2): 102-109, (Jun. 2013), 102-109.
Papagiannaros, A., et al., "Antitumor Activity of Doxorubicin Encapsulated in Hexadecylphosphocholine (HePC) Liposomes against Human Xenografts on Scid Mice", in vivo 20(1): 129-136 (2006), (Feb. 1, 2006), 129-136.
Abu Lila, Amr S., et al., "Targeting Anticancer Drugs to Tumor Vasculature Using Cationic Liposomes", Pharm Res, 27, (2010), 1171-1183.
Banerjee, Antara, et al., "Stearylamine-bearing cationic liposomes kill *Leishmania* parasites through surface exposed negatively charged phosphatidylserine", Journal of Antimicrobial Chemotherapy, 61, (2008), 103-110.
Fernandes, R. S., et al., "On the molecular mechanisms for the highly procoagulant pattern of C6 glioma cells", Journal of Thrombosis and Haemostasis, 4, (2006), 1546-1552.
Kenis, Heidi, et al., "Targeting Phosphatidylserine in Anti-Cancer Therapy", Current Pharmaceutical Design, 15, (2009), 1-5.
Kirszberg, Clarice, et al., "Simultaneous tissue factor expression and phosphatidylserine exposure account for the highly procoagulant pattern of melanoma cell lines", Melanoma Research, 19, (2009), 301-308.
Mayhew, E., et al., "Toxicity of Non-Drug-Containing Liposomes for Cultured Human Cells", Experimental Cell Research, 171, (1987), 195-202.
Riedl, Sabrina, et al., "In search of a novel target—Phosphatidylserine exposed by non-apoptotic tumor cells and metastases of malignancies with poor treatment efficacy", Biochimica et Biophysica Acta, 1808, (2011), 2638-2645.

(Continued)

*Primary Examiner* — Snigdha Maewall
(74) *Attorney, Agent, or Firm* — Schwegman Lundberg & Woessner, P.A.

(57) ABSTRACT

The present disclosure relates to the synergistic liposomal formulation comprising, phophatidylcholine, stearylamine and anticancer drugs for the treatment of cancer. The PC:SA cationic liposome encapsulated camptothecin (CPT) and doxorubicin (DOX) formulations show enhanced synergistic anti-cancer effect and provide improved therapeutic index as compared to either the liposome or drug alone. The present disclosure also relates to the use of Cationic liposomal preparation of phosphatidylcholine:stearylamine (PC:SA) showing anticancer effect. The SA-bearing liposome and drug entrapped in the liposome are effective against cancer both in vitro and in vivo, without causing any adverse effect on host.

12 Claims, 27 Drawing Sheets

(56) References Cited

OTHER PUBLICATIONS

Schröder-Borm, Hannah, et al., "The NK-lysin derived peptide NK-2 preferentially kills cancer cells with increased surface levels of negatively charged phosphatidylserine", *FEBS Letters*, 579, (2005), 6128-6134.

"Chapter 12.19 The clearance of apoptotic cells requires cellular interaction", *Cells*, Lewin, Benjamin, et al., Editors, Jones and Bartlett Publishers, Inc., Sudbury, MA, (2007), 553-554.

"World cancer factsheet. World cancer burden (2012)", © Copyright Cancer Research. International Agency for Research on Cancer, (Jan. 2014), 4 pgs.

Ahmed, H., et al., "Interaction and in vivo growth inhibition of Ehrlich ascites tumor cellsInteraction and in vivo growth inhibition of Ehrlich ascites tumor cells", *J. Biosci.*, 13(4) (Dec. 1988), 419-424.

Bandyopadhyay, Gautam, et al., "Chlorogenic acid inhibits Bcr-Abl tyrosine kinase and triggers p38 mitogen-activated protein kinase-dependent apoptosis in chronic myelogenous leukemic cells", *Blood*, 104, (2004), 2514-2522.

Banerjee, Antara, et al., "Complete Cure of Experimental Visceral Leishmaniasis with Amphotericin B in Stearylamine-Bearing Cationic Liposomes Involves Down-Regulation of IL-10 and Favorable T Cell Responses", *The Journal of Immunology*, 181, (2008), 1386-1398.

Basu, Mukul Kumar, "Site Specific Drug Delivery", H, K. Sen Memorial Lecture, *J. Inst. Chemists (India)*, vol. 82, Part 3, (2010), 65-73.

Beck, Adam W., et al., "Combination of a monoclonal anti-phosphatidylserine antibody with gemcitabine strongly inhibits the growth and metastasis of orthotopic pancreatic tumors", *Int. J. Cancer*, 118, (2006), 2639-2643.

Bhowmick, Swati, et al., "Comparison of liposome based antigen delivery systems for protection against Leishmania donovani", *Journal of Controlled Release*, 141, (2010), 199-207.

Burke, Thomas G., et al., "Liposomal Stabilization of Camptotbecin's Lactone Ring", *J. Am. Chem. Soc.*, 114, (1992), 8318-8319.

Chen, Yu Qing, et al., "A cationic amphiphilic peptide ABP-CM4 exhibits selective cytotoxicity against leukemia cells", *Peptides*, 31(8), (2010), 1504-1510.

Dalvit, Gabriel C., et al., "Reactive oxygen species in bovine embryo in vitro production", *Biocell*, 29(2), (2005), 209-212.

Drullion, C., et al., "Apoptosis and autophagy have opposite roles on imatinib-induced K562 leukemia cell senescence", *Cell Death and Disease*, 3, e373, (2012), 1-9.

Espinosa, Enrique, et al., "Classification on anticancer drugs—a new system based on therapeutic targets", *Cancer Treatment Reviews*, 29, (2003), 515-523.

Fanciullino, R., et al., "Liposome-Encapsulated Anticancer Drugs: Still Waiting for the Magic Bullet?", *Current Medicinal Chemistry*, 16, (2009), 4361-4373.

Frezard, F., "Liposomes: from biophysics to the design of peptide vaccines", *Braz J Med Biol Res*, 32(2), (1999), 181-189.

Fujimura, Taku, et al., "Inhibitory effect of the polyinosinic-polycytidylic acid/cationic liposome on the progression of murine B16F10 melanoma", *Eur. J. Immunol.*, 36, (2006), 3371-3380.

Ghosh, Debasree, et al., "Nanocapsulated curcumin: Oral chemopreventive formulation against diethylnitrosamine induced hepatocellular carcinoma in rat", *Chemico-Biological Interactions*, 195, (2012), 206-214.

Goldsby, Richard A., et al., *Immunology*, Fifth Edition, Freeman, W. H. & Company, (2002), 1-153.

Haidara, Khadidja, et al., "The flavonoid Casticin has multiple mechanisms of tumor cytotoxicity action", *Cancer Letters*, 242, (2006), 180-190.

Hanahan, Douglas, et al., "The Hallmarks of Cancer", *Cell*, 100, (2000), 57-70.

Hatefi, A., et al., "Camptothecin Delivery Methods", *Pharmaceutical Research*, 19(10), (Oct. 2002), 1389-1399.

Hung, Shih-Ya, et al., "Overexpression of Heme Oxygenase-1 Protects Dopaminergic Neurons against 1-Methyl-4-Phenylpyridinium-Induced Neurotoxicity", *Molecular Pharmacology*, 74, (2008), 1564-1575.

Idris, Aymen I., "Chapter 15—Analysis of Signalling Pathways by Western Blotting and Immunoprecipitation", *In: Bone Research Protocols, Methods in Molecular Biology*, vol. 816, Helfrich, Miep H., et al., Editors, (2012), 223-232.

Ilangovan, Raju, et al., "Inhibition of Apoptosis by Z-VAD-fmk in SMN-depleted S2 Cells", *The Journal of Biological Chemistry*, 278(33), (2003), 30993-30999.

Judy, Brendan F., et al., "Vascular Endothelial-Targeted Therapy Combined with Cytotoxic Chemotherapy InducesInflammatory Intratumoral Infiltrates and Inhibits Tumor Relapses after Surgery", *Neoplasia*,14(4), (Apr. 2012), 352-359.

Kim, Ryungsa, et al., "Cancer immunosuppression and autoimmune disease: beyond immunosuppressive networks for tumor immunity", *Immunology*, 119, (2006), 254-264.

Lowry, Oliver H, et al., "Protein Measurement With the Folin Phenol Reagent", *Journal of Biological Chemistry*, 193, (1951), 265-275.

Miller, Aaron, et al., "Sialic Acid Content of the Erythrocyte and of an Ascites Tumor Cell of the Mouse", *Cancer Research*, vol. 23, (Mar. 1963), 485-490.

Mondal, Smriti, et al., "A Curative Immune Profile One Week after Treatment of Indian Kala-Azar Patients Predicts Success with a Short-Course Liposomal Amphotericin B Therapy", *PLoS Negl Trop Dis* 4(7): e764, (Jul. 2010).

Morgan, Meredith T., et al., "Dendrimer-Encapsulated Camptothecins: Increased Solubility, Cellular Uptake, and Cellular Retention Affords Enhanced Anticancer Activity In vitro", *Cancer Research*, 66(24), (2006), 11913-11921.

Nie, Yu, et al., "Cholesterol Derivatives Based Charged Liposomes for Doxorubicin Delivery: Preparation, In Vitro and In Vivo Characterization", *Theranostics*, 2(11), (2012), 1092-1103.

Ozaslan, Mehmet, et al., "Ehrlich ascites carcinoma", *African Journal of Biotechnology*, 10(13), (2011), 2375-2378.

Saetern, Ann Mari, et al., "A Method to Determine the Incorporation Capacity of Camptothecin in Liposomes", Article 40, *AAPS PharmSciTech*, 5(3), (2004), 1-8.

Sen, N., et al., "Camptothecin induced mitochondrial dysfunction leading to programmed cell death in unicellular hemoflagellate *Leishmania donovani*", *Cell Death and Differentiation*, 11, (2004), 924-936.

Shiratsuchi, Akiko, et al., "Phosphatidylserine-Mediated Phagocytosis of Anticancer Drug-Treated Cells by Macrophages1", *J. Biochem.*, 126, (1999), 1101-1106.

Stebelska, K., et al., "The Effect of PS Content on the Ability of Natural Membranes to Fuse with Positively Charged Liposomes and Lipoplexes", *J. Membrane Biol.*, 206, (2005), 203-214.

Thorn, Caroline F., et al., "Doxorubicin pathways: pharmacodynamics and adverse effects", NIH Public Access, Author Manuscript, Published in final edited form as: *Pharmacogenet Genomics*, 21(7) (2011), 440-446, (2011), 12 pgs.

Tu, Shui Ping, et al., "Induction of apoptosis by arsenic trioxide and hydroxy camptothecin in gastriccancer cells in vitro", *World J Gastroentero*, 6(4), (2000), 532-539.

Utsugi, Teruhiro, et al., "Elevated Expression of Phosphatidylserine in the Outer Membrane Leaflet of Human Tumor Cells and Recognition by Activated Human Blood Monocytes", *Cancer Research*, 51, (1991), 3062-3066.

Youssef, Magda I., et al., "Expression of Ki 67 in hepatocellular carcinoma induced by diethylnitrosamine in mice and its correlation with histopathological alterations", *Journal of Applied Pharmaceutical Science*, 02 (03), (2012), 52-59.

Nussbaumer, Susanne, "Analysis of anticancer drugs: A review", *Talanta* 85, (2011), 2265-2289.

Li, Jing, et al., "A review on phospholipids and their main applications in drug delivery systems", Asian Journal of Pharmaceutical Sciences 10 (2015), (Sep. 28, 2014), 81-98.

\* cited by examiner

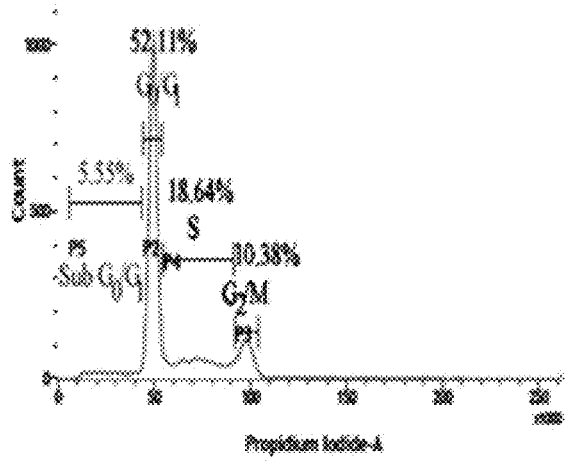
(a)
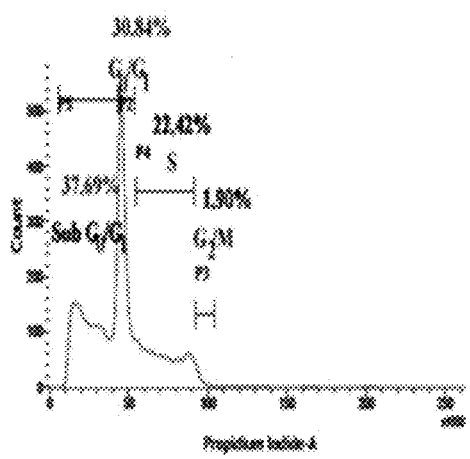
(b)
FIGURE 9(B)

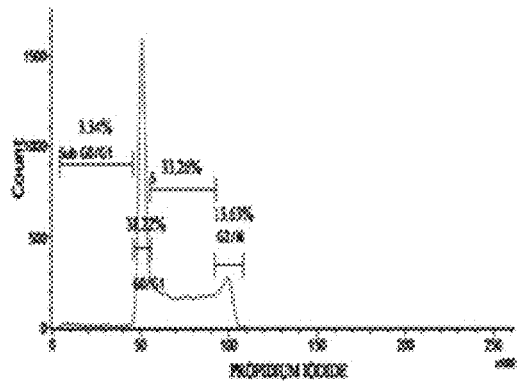
(a)
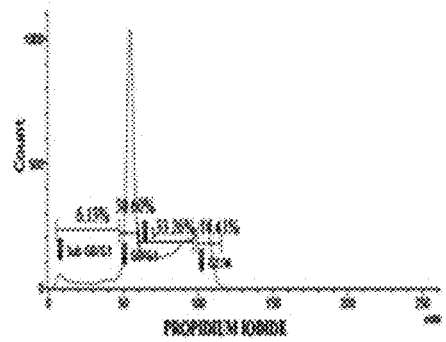
(b)
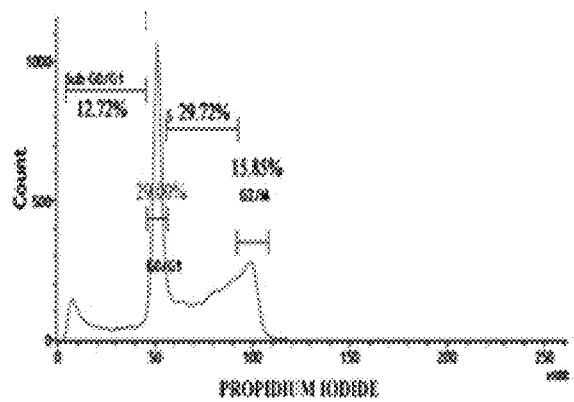
(c)
FIGURE 9(C)

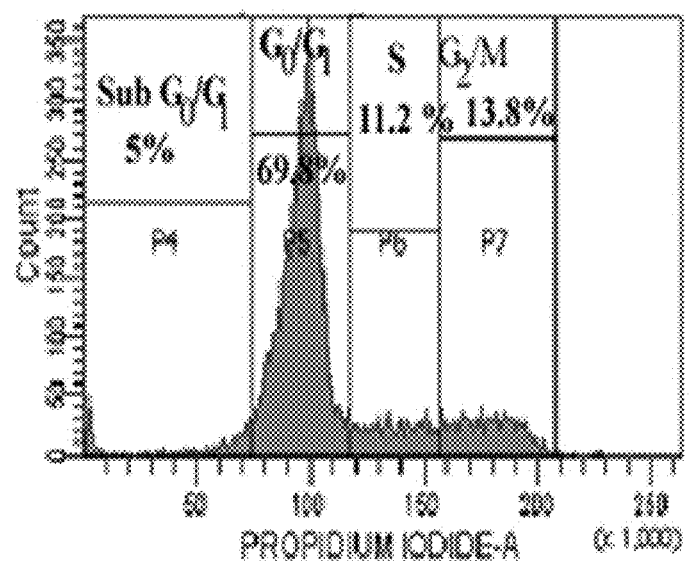
(a)
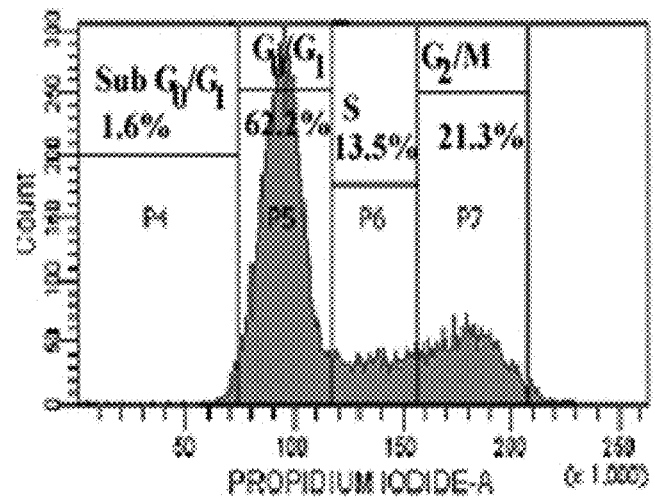
(b)
FIGURE 9(D)

(a) (b)

(a) (b)

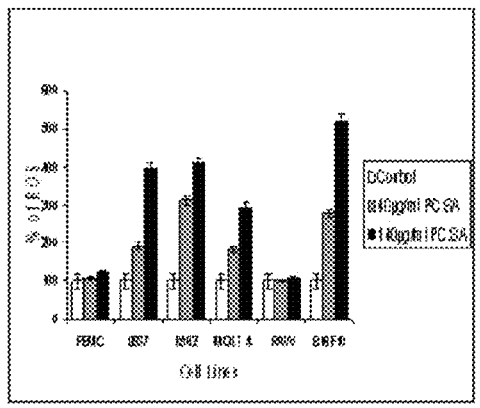
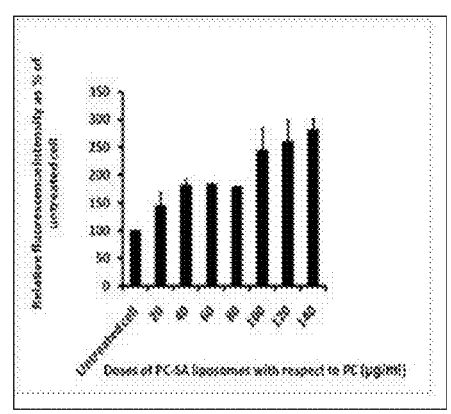
FIGURE 10(A)    FIGURE 10 (B)
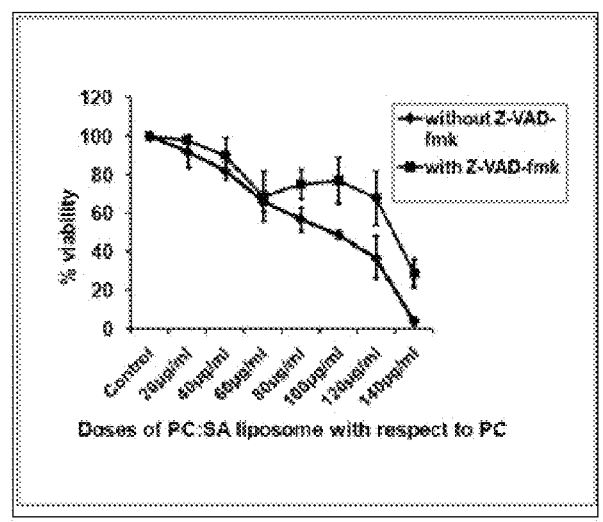
FIGURE 11

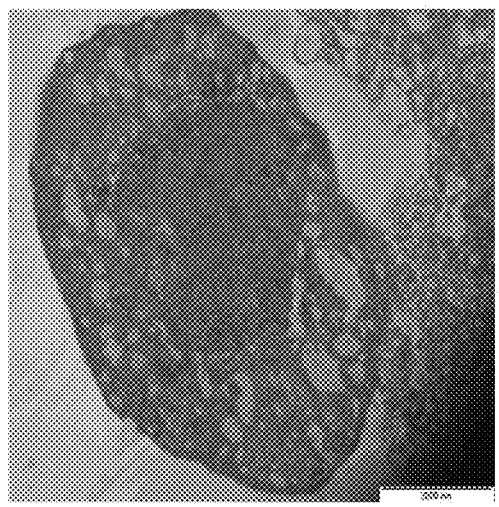
(a)
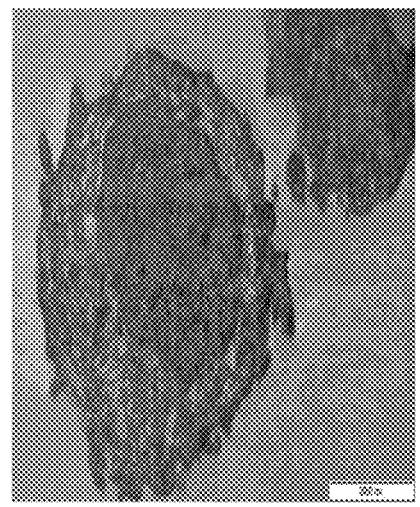
(b)
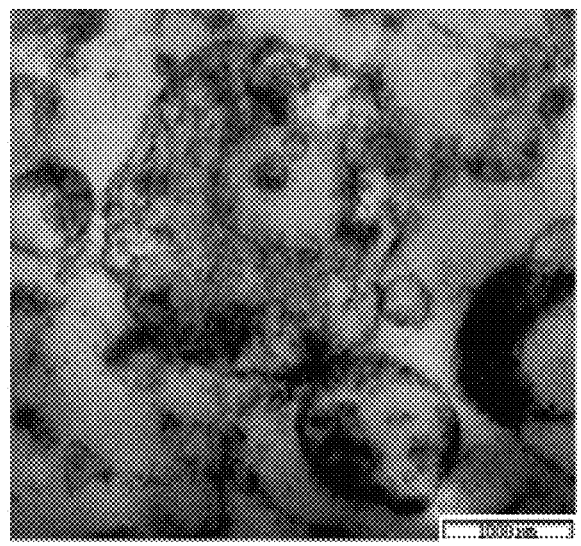
(c)
FIGURE 12

FIGURE 15 (A, B, C)
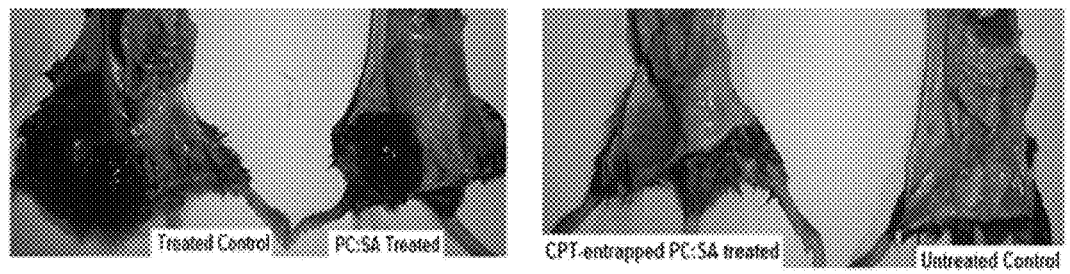
FIGURE 16(A)
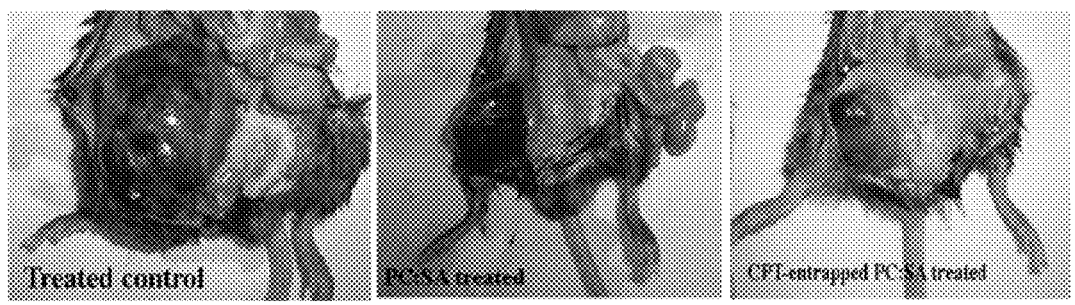
FIGURE 16(B)

SYNERGISTIC LIPOSOMAL FORMULATION FOR THE TREATMENT OF CANCER

PRIORITY CLAIM TO RELATED APPLICATIONS

This application is a U.S. national stage application filed under 35 U.S.C. § 371 from International Application Serial No. PCT/IN2014/000610, which was filed 18 Sep. 2014, and published as WO2015/040636 on 26 Mar. 2015, and which claims priority to India Application No. 2756/DEL/2013, filed 19 Sep. 2013, which applications and publication are incorporated by reference as if reproduced herein and made a part hereof in their entirety, and the benefit of priority of each of which is claimed herein.

FIELD OF THE INVENTION

The present disclosure relates to a synergistic liposomal formulation. The stearylamine bearing cationic liposome is shown to be very effective against the treatment of the disease cancer, and when anticancer drug camptothecin is encapsulated into the cationic liposome, then the formulation shows anticancer property which is far more effective than either the liposome or the drug alone.

BACKGROUND OF THE INVENTION

A major difficulty of targeted drug delivery against cancer is the lack of ubiquitously expressed tumour-specific antigen or receptor. However, it has now been established that the phospholipid, Phosphatidylserine (PS) can be exploited as a potential target for drug delivery against cancer.

PS is a phospholipid that under normal conditions resides almost exclusively in the inner leaflet of the plasma membrane. PS asymmetry is maintained by an ATP-dependent amino phospholipid translocase that is responsible for inward movement of the aminophospholipids. Loss of the PS asymmetry is observed under different pathologic and physiologic conditions, including programmed cell death, cell aging, cell migration, cell degranulation (1). Spontaneous PS exposure has been observed in many malignant cell types in the absence of exogenous activators or cell injury (2). Surface PS exposure is observed in solid tumors and tumor vasculature and can be a marker of tumor vasculature (3). PS-expressing tumor endothelium was mostly found to be non-apoptotic. The factors like hypoxic reoxygenation, inflammatory cytokines, acidity, all mostly prevalent factors in tumorigenesis, are mainly the cause of PS exposure. Recent studies have shown that tumorigenic, undifferentiated murine erythroleukemia cell expresses 7-8 fold more PS in their outer leaflet than their differentiated counterparts (2). Elevated expression of surface PS is also found in human melanoma and lung carcinoma (4). Hence, PS on tumor vessels is an attractive target for cancer imaging and therapy. Reports have shown that anti-cancer drugs have been prepared exploiting the elevated PS level of the cancer cells which serves as a marker. NK-lysin derived peptide NK-2 preferentially kills cancer cells. The selectivity of the cationic membranolytic peptide NK-2 has been assigned to the differences in the membrane phospholipid composition of target cancer cells (5). PS exposure is neither of apoptotic nor of experimental artificial origin (6). Anti-phosphatidylserine antibodies have also been used in cancer therapy (7). Hence, it is suggested that the SA-bearing liposomes may prove to be effective in anti-cancer therapy. Since the drug-free liposome itself selectively recognizes and destroys elevated PS exposed on membrane surfaces, this property of the liposome can be utilized in anticancer therapeutic strategies. The SA-bearing liposome has been shown to cause immunomodulation in the host and targets PS-bearing parasites for destruction (8). It is evident that the SA-bearing liposomes should effectively target the cancer cells. Moreover, the efficacy of the anticancer drugs which target the surface PS of the tumor cells and also otherwise shall profoundly increase when administered entrapped in these liposomal formulations. The anticancer drugs frequently affect the normal cells and thus cause severe side effects. But, when administered in a liposomal covering shall thus decrease the cytotoxicity. We can also ensure effective and selective targeting of the anti-cancer drugs when administered within this SA-bearing liposome because PS on the tumor vessels is abundant and is on the luminal surface of the tumor endothelium. This renders it directly accessible for binding by any vasculature targeting agents in the blood. Moreover, it is present on a high percentage of tumor endothelial cells in diverse solid tumors; and it is absent from endothelium in all normal tissues examined to date, thus ensuring selectivity. The phenomenon of PS exposure is not exclusively associated with apoptosis. For instance monocytes differentiating into macrophages and a subpopulation of T-lymphocytes expose PS. Living tumour cells and endothelial cells of the tumour blood vessels also express high levels of PS on their surface. Furthermore cell surface exposure of PS is independent of cell type and thus independent of the type of cancer (3). Vascular-targeted strategies directed against exposed PS may be a powerful adjunct to postoperative chemotherapy in preventing relapses after cancer surgery (9). It has also been shown that B16F10 murine melanoma cells express high levels of PS on their surfaces (10). These features support the proposal that PS can be utilized as an attractive target for the tumour blood vessels as well as the living tumour cells. Liposomes are under extensive investigation as targeted drug delivery against many diseases because the drug here is protected from bioenvironment and thus remains stable for a much longer time. They are small concentric bilayered vesicles, in which an aqueous volume is entirely enclosed by a membranous lipid bilayer mainly composed of natural or synthetic phospholipids. The first generation of liposomes, a.k.a. conventional liposomes, was developed in the early 70's. They were composed of phosphatidylcholine, phosphatidylserine, phosphoglycerol, and cardiolipine associated with cholesterol so as to reduce permeability (11).

Liposomal Drug Delivery System:

Lipid associated formulations have been proved to be more effective therapies with much lesser toxicity against in vitro and in vivo anti-protozoan activity e.g. visceral leishmaniasis (VL). The advantage of such formulations is their ability to concentrate high levels of drugs in the infected target organs. For example, AmBisome, a liposomal formulation of amphotericin B, is the safest and can be administered at doses much higher than the free form of the drug with much less toxicity (12). The drug-free stearylamine (SA)-bearing cationic liposomes have in vitro activity. A single dose of the drug entrapped in this cationic liposome formulations has a synergistic activity and hence a much more profound effect on the target. The profound effect of the drug-free liposome is due to recognition of the phosphatidylserine (PS) on the parasite membrane by the SA liposomes. The study of the mode of action of the SA-bearing cationic liposomes revealed that the recognition of the surface PS by the liposome is necessary for its ability to damage the parasite membrane resulting in its ultimate death (12). This peculiar mode of action of the drug-free liposomes leads to an interesting hypothesis. SA:PC:Chol in its molar ratio 1:4:5 was found to be toxic for cancer-derived and normal human cultured cell lines at varying degrees (11). Cationic liposomes are used as a delivery system to cells of compounds capable of silencing a target protein and enzyme substrate and also used for detecting inhibitory activity of a target protein in a cell as well as signal transduction pathway in a cell (15).

Classification of Liposomes:

The properties of liposomes vary substantially with lipid composition, size, surface charge and method of preparation. Liposomes can be either classified following in the following manner:

According to Size or Lamellarity

Small Unilamellar Vesicles (<100 nm, a.k.a. SUV) are surrounded by a single lipid bilayer of 25-100 nm diameter. Large Unilamellar Vesicles (100-500 nm, a.k.a. LUV) are a heterogeneous group of vesicles similar to SUVs and are surrounded by a single lipid bilayer. Finally, Multilamellar Vesicles (>500 nm, a.k.a. MLV) consist of several lipid bilayers separated from each other by a layer of aqueous solution. They have onion like structures (11).

According to on the Method of Preparation

Reverse Phase Evaporation Vesicle (REV):

The reverse-phase evaporation technique, the first to use 'water-in-oil' emulsions, encapsulates up to 50% of solute. Preparation of reverse-phase evaporation vesicles (REV) consists of a rapid injection of aqueous solution into an organic solvent which contains the lipids dissolved. Thus, following the formation of water droplets ('water-in-oil' emulsion) by bath sonication of the two-phase mixture, the emulsion is dried down to a semi-solid gel in a rotary evaporator. The next step is to subject the gel to vigorous mechanical shaking to induce a phase change from a water-in-oil emulsion to a vesicle suspension. In these circumstances, some water droplets collapse, and these droplets attach to adjacent, intact vesicles to form the outer leaflet of the bilayer of a large unilamellar liposome (diameter in the range of 0.1 to 1 µm) (16).

Dehydration-Rehydration Vesicles (DRV):

Another method that produces dehydration-rehydration vesicles (DRV) is both simple and easy to scale up, and usually gives high yields of solute entrapment (up to 80%). Preparation of DRV consists of mixing an aqueous solution of the solute with a suspension of 'empty' (water-containing) liposomes and freeze-drying the resulting, mixture. The intimate contact of flattened liposomal membrane structures and solute molecules in a dry environment and the fusion of membranes caused by dehydration facilitates the incorporation of solute during the controlled rehydration steps. Separation of solute-containing DRV from unentrapped solute can be carried out by centrifugation easily if needed. Vesicles formed by the dehydration-rehydration technique are multilamellar with heterogeneous sizes (diameters varying from 0.1 to 2.0 µm) (16).

Multilamellar Vesicles (MLV):

The most easily prepared and processed liposomal form is Multilamellar vesicles or MLVs. MLVs are prepared by first casting a lipid film in organic solvent (chloroform). Then lipid particles are dispersed in aqueous solvent followed by probe sonication. This form of liposome has advantages over both DRV and REV form of liposome due to its optimum size (200-250 nm) and multilamellar structure which allows higher amount of drug to be successfully entrapped into the liposome. The MLV form of liposome showed maximum efficacy in the present model and highest drug entrapment efficacy. Hence, most of the experiments were performed with this particular form of liposome.

According to In Vivo Application:

Conventional liposomes which may be neutral or negatively charged. They are used mainly for macrophage targeting or for vaccination. Stealth (stearically stabilized) liposomes which carry polymer coatings to obtain prolonged circulation times. Immunoliposomes (antibody targeted) are used for specific targeting and Cationic liposomes are employed mainly for gene delivery or cancer therapy. Liposomes containing cationic lipids (DOTAP:DOPE, SA) have been widely used as transfection mediators both in vitro and in vivo due to their ability to interact with negatively charged molecules such as DNA and phosphatidylserine of cell membranes. The amphiphilic properties of cationic lipid molecules together with positive charge and defined phase behaviour of liposomes composed of them, make possible interactions such as adsorption, fusion, poration and destabilization with negatively charged membranes. Some cationic lipids are able to penetrate natural membranes and localize in the inner leaflet, forming invaginations and even endosome-like vesicles. The initial event occurring between cationic liposomes and negatively charged plasma membrane is adsorption. Electrostatic and hydrophobic interactions may lead to hemifusion, fusion, poration or, alternatively, receptor-mediated endocytosis may occur (17).

Biomembrane mimetic model system were prepared with PC:PS, PC:PA or PC:Chol liposomes and it was found that PC:SA liposomes had specific affinity for PC:PS liposomes rather than PC:Chol or anionic PC:PA liposomes. This further supported the PC:SA liposome interacted mainly with PS. This indicates that the SA-bearing liposomes can be used as a valuable delivery system against cancer cells which also have elevated levels of negatively charged PS on the outer surface of their membranes (12). Even in cationic liposomes variations can be made on the basis of methods of preparation. Previously, work has been done on comparative study of these different types of liposomes and their antigen entrapment efficiency with *Leishimania donovani* promastigote membrane antigens (LAg). In that study mice were immunized with LAg encapsulated in multilamellar vesicles (MLV), dehydration-rehydration vesicles (DRV) and reverse-phase evaporation vesicles (REV) and were challenged with parasites ten days after vaccination. Leishmanial antigen (LAg) in MLV or DRV induced almost complete protection, while LAg alone or entrapped in REV exhibited partial resistance. MLV encapsulated LAg demonstrated durable cell-mediated immunity and mice challenged ten weeks after vaccination could also resist experimental challenge strongly (18).

Selecting an Appropriate Antineoplastic Agent:

Most patients with advanced solid tumours still die of their disease. For this reason, new effective drugs are needed. A number of anticancer drugs are under investigation at present which target the tumor cell at DNA or protein level. Other elements interacting with tumors like the endothelium or extracellular matrix may also be targeted.

Camptothecin (CPT) is a quinoline alkaloid isolated from the bark and stem of *Camptotheca acuminata* (Camptotheca, Happy tree), a tree native to China (19). It exhibits potent cytotoxic activity against a range of tumor cell lines CPT, possesses a high melting point (264-267° C.), and has a molecular weight of 348.11 obtained by high-resolution mass spectroscopy, corresponding to the formula ($C_{20}H_{16}N_2O_4$). Camptothecin inhibits both DNA and RNA synthesis in mammalian cells. The inhibition of RNA synthesis results in shortened RNA chains and is rapidly reversible upon drug removal while inhibition of DNA synthesis is only partially reversible. CPT binds to Topoisomerase 1 and DNA complex (with Hydrogen bonds), resulting in a stable ternary complex. Topoisomerases are a family of enzymes which relax supercoiled DNA by making transient single stranded breaks in the DNA, allowing the uncut strand to pass through the break before resealing the nick (thus increasing its linking number by 1). Binding of CPT inhibits this rejoining step which ultimately leads to DNA fragmentation and apoptosis. This drug is widely distributed in the body including the central nervous system, lungs and liver (20).

Camptothecin encloses in its structure a highly conjugated pentacyclic ring with an α-hydroxylactone portion at carbon 12 which is essential for its in vitro and in vivo antitumor activity. Unfortunately this lactone ring is highly susceptible to hydrolysis and under physiological conditions i.e., at pH 7 or above, the lactone ring readily opens to yield the inactive carboxylate form of the drug (20). Ring opening of camptothecin is thought to result in a loss of activity due to the following three reasons. First, the carboxylate form displays decreased association with the membrane. Second, ring opening results in a charged drug species which exhibits limited diffusibility through lipid bilayer domains. Third, evidence from cell-free experiments indicates that ring opening results in significantly reduced intrinsic potency towards the topoisomerase-1 target.

The above drawback along with poor water solubility and high adverse drug reaction limits the application of CPT in therapeutics. For this reason different lipid based formulations were investigated and it was found that CPT is soluble in various lipids and also biologically active at the same time. Two types of spectroscopic data are available which support that liposome associated camptothecin is stable. The first evidence comes from, where there is a blue shift in the drug's emission spectrum which is observed upon its association with membrane. Such a spectral shift is indicative of a change in the dielectric constant of the medium surrounding the fluorophore, as when a compound leaves an aqueous environment and intercalates in between the lipid acyl chains (21). Thus, liposomal drug delivery systems are of potential utility for introducing camptothecin (or related lipophillic analogues) in its stable and pharmacologically active form to cancer victims.

Doxorubicin (DOX) is another an important class of drug that is used in cancer therapy. It is an anthracycline antibiotic. It is photosensitive in nature. It was first extracted from *Streptomyces peucetius*. It is used in the treatment of several cancers that include breast cancer, lung, ovarian, gastric, Hodgkin's and Non Hodgkin's lymphoma, Multiple myeloma and sarcoma and pediatric cancers. The main function of doxorubicin is in intercalating DNA. There are two proposed mechanisms by which doxorubicin acts on cancer cells. They are (i) Intercalation into DNA and disruption of topoisomerase II mediated DNA repair and (ii) Generation of free radicals and their disruption of cell membrane and damage to DNA and proteins. In other words doxorubicin is oxidized to semiquinone (an unstable metabolite) which is converted back to doxorubicin in a process that releases reactive oxygen species (ROS). ROS have the ability to cause lipid peroxidation and membrane damage, DNA damage, oxidative stress, and stimulates apoptic pathways of cell death. Doxorubicin can enter the nucleus, poison DNA topoisomerase II and cause damage to the DNA and cell death. A major limitation for the use of doxorubicin is cardiotoxicity, with the total cumulative dose being the only criteria currently used to predict the toxicity (22).

The present invention claims that cationic liposome in all its three forms (MLV, DRV, REV) is a potential anticancer agent which selectively targets the cancer cells through the cancer cell surface exposed phosphatidylserine. The formulation has no adverse effects on the normal cells and hence is a successful targeted therapy against cancer. The anticancer drug encapsulated formulations had significant anticancer effect both in vitro and in vivo. The drug encapsulated liposome has a synergistic effect and hence shall be effective in bringing down the dosage of the drug and thus protecting against chemotherapeutic toxicity. The liposomal formulation is successful in controlling the adverse chemotherapeutic effect of anti-cancer drugs due low dosage of application with high efficacy and targeted delivery with minimum damage to normal cells. The formulation mainly works through the intrinsic kinase signalling pathway of the cancer cells. It can be a valuable therapeutic agent since it showed negligible therapeutic toxicity and miraculous therapeutic efficiency in vivo.

OBJECTIVES OF THE INVENTION

The main objective of the present disclosure is to provide a synergistic liposomal formulation comprising of PC:SA and anticancer drug.

Another object of the present disclosure is to provide a formulation comprising: phophatidylcholine, stearylamine and camptothecin in a molar ratio of 7(PC):2(SA):0.7(CPT).

Yet another object of the present disclosure is to provide a formulation prepared in the form of dehydration-rehydration vesicles (DRV), reverse phase evaporation vesicle (REV) and multilamellar vesicles (MLV).

Still another object of the present disclosure is to provide the use of phosphatidylcholine (PC) and stearylamine (SA) in a molar ratio of 7:2, for the treatment of cancer.

Another object of the present disclosure is that PC:SA liposome-induced killing of cancer cells is due to apoptosis, dissipation of mitochondrial membrane potential, increased level of reactive oxygen species (ROS).

Yet another object of the present disclosure is to reduce the side effect the drugs thus improving their therapeutic efficacy.

SUMMARY OF THE INVENTION

Accordingly, the present disclosure provides, a synergistic liposomal formulation for the treatment of cancer wherein the formulation comprises, phophatidylcholine, stearylamine and anticancer drugs.

In an embodiment of the present disclosure, the anticancer drugs are selected from the group consisting of camptothecin (CPT), doxorubicin (DOX), cisplatin or paclitaxel.

In still another embodiment of the present disclosure, the ratio of phatidylcholine, stearylamine and camptothecin in synergistic liposomal formulation is 7(PC):2(SA):0.7(CPT).

In yet another embodiment of the present disclosure, the ratio of phatidylcholine, stearylamine and doxorubicin in the synergistic liposomal formulation is 7(PC):2(SA):0.5 (DOX).

In still another embodiment of the present disclosure, the formulation is prepared in the form of dehydration-rehydration vesicles (DRV), reverse phase evaporation vesicle (REV) and multilamellar vesicles (MLV).

In yet another embodiment of the present disclosure, the formulation is used for the treatment of murine melanoma, rat glioma, colorectal adenocarcinoma, human colon carcinoma, chronic myelogenous leukemia, acute lymphoblastic leukemia and ascites carcinoma in vitro.

In still another embodiment of the present disclosure, the dose of the synergistic liposomal formulation is used at 20-140 µg/ml with respect to PC.

Yet another embodiment of the present disclosure provides the use of liposomal formulation for the treatment of cancer, wherein the said formulation comprises of phosphatidylcholine (PC) and stearylamine (SA) in a molar ratio of 7:2.

Still another embodiment of the present disclosure, the EC50 value of the liposomal formulation against cancer cell lines is in the range of 60-80 µg/ml. In yet another embodiment of the present disclosure, the dosage of the liposomal formulation is administered at 3 doses of 800 mg/Kg body weight (intravenously) with respect to PC against DEN induced hepatocarcinoma in rats.

In still another embodiment of the present disclosure, the dosage of the liposomal formulation is administered at a single shot injection of 1.7 g/Kg body weight with respect to PC (intravenously and intra-peritoneally) in Swiss albino mice to inhibit growth of all the cell types was measured by inhibition of 3-(4, 5-dimethyl-thiozol-2-yl)-2,5-diphenyltetrazolium bromide (MTT) reduction to insoluble formazan by mitochondrial dehydrogenase. Error bars denote standard deviation of 3 experiments.

FIG. 3: Effect of activity of PC:SA liposome after blocking it with different doses of PC:PS and PC:Chol liposome. PC:SA liposomes (120 µg/ml with respect to PC) were incubated for 30 min with different concentrations of PC:PS or PC:Chol liposomes (15-240 µg/ml with respect to PC) prior to incubation with 5≅10 ml of B16F10 (A). K562 (B), U937 (C) and rat C6 glioma cells (D). After 120 min post-treatment the viability was measured by MTT assay. Data points represent the mean of triplicate samples±SEM from a single experiment, representative of three different experiments.

FIG. 4: Blocking of killing activity of PC:SA liposome by annexin V. Cells were incubated with or without purified recombinant annexin V (5 µg/1×$10^5$ cells) for 30 min in annexin V binding buffer, washed with 20 mM PBS and resuspended in respective media supplemented with 10% FCS. K562 cells were treated with 140 µg/ml of PC:SA liposome with respect to PC (A) and B16F10 cells were treated with graded concentrations (20-140 µg/ml) of PC:SA and PC:Chol liposomes (B). Cells were washed with 20 mM PBS and resuspended in DMEM medium supplemented with 10% FCS. The viability of the cells was determined by MTT assay after 120 min.

FIG. 5: Comparison of the effect of camptothecin (CPT) entrapped in PC:SA liposome with respect to PC (20-140 µg/ml) and free CPT (1-7 µg/ml, same concentrations that were entrapped in the liposomes) for 2 h on B16F10, EAC, human PBMC, SW480, 0937 and rat C6 glioma cells (5×$10^5$/ml). All cell lines were treated with MLV form of PC:SA liposome except where mentioned. B16F10 cells were treated with graded doses of CPT entrapped in MLV, DRV and REV forms of PC:SA liposomes (A). EAC (C), rat C6 glioma (E), human PBMC of healthy donor (G), SW480 (I) and U937 (K) cells were treated with graded doses of CPT entrapped in PC:SA liposome. B16F10 (B), EAC (D), rat C6 glioma (F), human PBMC of healthy donor (H), SW480 (J) and U937 (L) were treated graded doses of CPT. The viability was measured by MTT assay.

FIG. 6: Comparison of the effect of doxorubicin (DOX) entrapped in MLV PC:SA liposome with respect to PC (20-140 µg/ml) and free DOX (1-7 µg/ml, same concentrations that were entrapped in the liposomes) for 2 h on U937, rat C6 glioma and EAC cells (5×$10^5$/ml). U937 (A), rat C6 glioma (C) and EAC (E) cells were treated with graded doses of DOX entrapped in PC:SA liposome. U937 (B), rat C6 glioma (D) and EAC (F) cells were treated with graded doses of DOX. The viability was measured by MTT assay.

FIG. 7: Apoptotic effect of PC:SA liposome (140 µg/ml with respect to PC) on different cell lines (5×$10^5$ cells/nil). A: B16F10 cells-untreated (a), treated for 2 h (b). B: K562 cells-untreated (a), treated for 2 h (b) and 4 h (c). C: U937 cells-untreated (a), treated for 2 h (b). D: MOLT4 cells-untreated (a) and treated for 4 h (c). E: Human PBMC from healthy donor-untreated (a) and treated for 4 h (b). Annexin

Figure 1A:
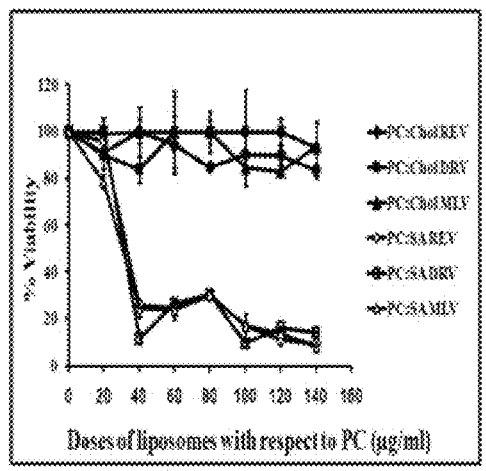
FIG. 1: In vitro cytotoxic effect of graded doses (20-140 µg/ml with respect to PC) of cationic (PC:SA), neutral (PC:Chol) and anionic (PC:PS) liposomes on different cell lines (5×$10^5$/ml) after 2 h of treatment. B16F10, rat brain astrocytes, rat C6 glioma, SW480, HCT116 and HepG2 cell lines were cultured in DMEM medium supplemented with 10% FCS with graded concentrations of different liposomes. RAW 264.7, K562, MOLT4, U937 cell lines, Ehrlichs ascites carcinoma cells and human PBMC of healthy donors were cultured in RPMI medium supplemented with 10% FCS with graded concentraions of different liposomes. The cell lines were treated with MLV form of liposomes except where mentioned. B16F10 cells were treated with PC:SA (MLV, REV and DRV), PC:Choi (MLV, REVand DRV) liposomes (A). RAW 264.7 cells were treated with PC:SA (MLV, REV and DRV) liposomes (B). K562 cells were treated with PC:SA, PC:Chol and PC:PS liposomes (C). U937 cells (D), Rat C6 glioma (F), rat brain astrocytes obtained from cerebral cortex of zero day old rats cells (G) were treated with PC:SA and PC:Chol liposomes. Human PBMC of normal donors (E), Ascites carcinoma cells obtained from mouse peritoneal fluid (H), SW480 (1), HCT 116 (J) and HepG2 cells (K) were treated with PC:SA liposomes. The viability of all the cell types was measured by inhibition of 3-(4, 5-dimethylthiozol-2-yl)-2, 5-diphenyltetrazolium bromide (MTT) reduction to insoluble formazan by mitochondrial dehydrogenase. Error bars denote standard deviation of 3 experiments.

V-PI binding assay was then performed using annexin V-FITC apoptosis detection kit followed by analysis in a flow cytometer. Values in the quadrants represent percent positive cells.

FIG. 8: Depolarization of mitochondrial membrane potential. Effect of PC:SA (140 µg/ml with respect to PC), CPT (7 µg/ml) and 7 µg/ml CPT entrapped in 140 µg/ml of PC:SA liposomes on different cell lines for 2 h treatment. A: B16F10 cells-untreated (a), treated with CPT (b), PC:SA (c) and CPT entrapped in PC:SA liposomes (d). B: K562 cells-untreated (a), treated with PC:SA liposome (b). The cells after treatment were stained with the mitochondrial membrane potential-sensitive dye JC-1 and analyzed in a flow cytometer. The percentage of cells expressing green and red fluorescence is indicated.

FIG. 9: DNA cell cycle analysis (apoptotic nuclei [Sub $G_0/G_1$ peak] and $G_2/M$ arrest) by flowcytometry using PI stain. Different cell lines ($5 \times 10^5$/ml) were treated with 140 µg/ml of PC:SA with respect to PC, washed twice in PBS. Pelleted cells were fixed in 70% cold ethanol and incubated overnight at $-20°$ C. After two washes in PBS the cells were resuspended in 0.5 ml of PI containing RNaseA and the mixture was incubated for 20 min in the dark at room temperature. The fluorescence intensity of PI was analysed with a FACS Calibur flow cytometry and Cell Quest software. A: B16F10 cells-untreated (a) and treated for 2 h (b). Gates were set to assess the percentage of dead sub $G_0/G_1$ (P4), $G_0/G_1$ (P5), S (P6) and $G_2M$ (P7). B: K562 cells-untreated (a) and treated for 2 h (b). Gates were set to assess the percentage of dead Sub $G_0/G_1$ (P5), $G_0/G_1$ (P2), S (P4) and $G_2M$ (P3). C: U937 cells-untreated (a), treated for 2 h (b) and 4 h (c). Gates were set to assess the percentage of dead Sub $G_0/G_1$, $G_0/G_1$, S and $G_21M$ arrest. D: MOLT4 cells-untreated (a), treated for 4 h (b). Sub $G_0/G_1$ (P4), $G_0/G_1$ (P5), S (P6) and $G_2M$ arrest (P7). E: RAW 264.7 cells-untreated (a), treated for 2 h (b). Sub $G_0/G_1$ (P4), $G_0/G_1$ (P5), S (P6) and $G_2M$ (P7). F: Human PBMC of healthy donor-untreated (a), treated for 2 h (b). Sub $G_0/G_1$ (P4), $G_0/G_1$ (P5), S (P6) and $G_2M$ (P7). Bars denote boundaries of cell cycle.

FIG. 10: Determination of PC:SA liposome induced ROS generation. K562, MOLT4, U937 and normal human PBMC were treated with 40 and 140 µg/ml of PC:SA with respect to PC for 4 h and B16F10 and RAW 264.7 cells were treated with same concentrations of PC:SA liposome for 2 h (A), K562 cells were treated with graded concentrations of PC:SA liposome (20-140 µg/ml) for 2 h (B). ROS was measured in treated and untreated cells incubated in the fluorescence dye H2DCFDA (1 µM) for 30 min at 31° C. by fluorescence spectrophotometer. Data are expressed as mean of ±SEM of three independent experiments.

FIG. 11: PC:SA liposome induces caspase dependent cell death. K562 cells were treated with graded doses of PC:SA liposome (20-140 µg/ml with respect to PC) in the presence or absence of pancaspase inhibitor Z-VAD-fmk (10 µM). The reduction in the viability of cells was determined by MTT assay. Data points represent the mean of triplicate samples±SEM from a single experiment.

FIG. 12: Transmission electron microscopy of U937 cells treated with PC:SA liposomes. U937 cells were incubated for 4 h under standard conditions with medium alone (a), 40 µg/ml (b) and 140 µg/ml (c) of PC:SA liposomes with respect to PC. Three representatives of electron micrographs of untreated (a), 40 µg/ml of PC:SA treated (b) cells revealed disruption of membrane integrity, and 140 µg/ml of PC:SA treated (c) extensive vacuolization and membrane breakage as well as depletion of electron-dense cytoplasmic material indicating that cell death is in process. Scale bars: 2000 nm (a and b), 1000 nm (c).

FIG. 13: Immunoblot-based demonstration of the involvement of p21 (a), ERK (b), p-ERK (c), caspase 8 (d), cleaved caspase 9 (e) and cleaved caspase 3 (f) in PC:SA (140 µg/ml with respect to PC) treated RAW264.7 (left column) and B16F10 (right column) cell lines. β-actin was used as loading control (g) (A). Involvement of p-ERK (top panel) and Bid (middle panel) in PC:SA (20-140 µg/ml with respect to PC) treated U937 cell line. β-actin was used as loading control (bottom panel) (B). 2 h treated were harvested, lysed, and equivalent amount of lysates were separated by SDS-PAGE and electrotransferred. The membranes were probed with anti-ERK, anti-phospho-ERK, anti-caspase 8, anti-cleaved caspase 9, anti-p21, anti-Bid and anti-β Actin antibodies.

Figure 14:
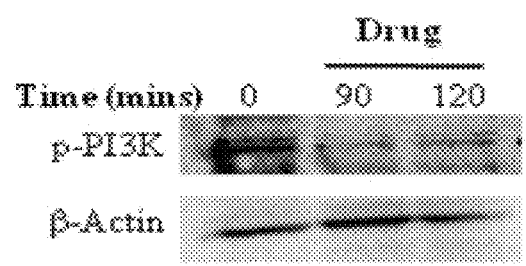

FIG. 14: Immunoblot-based determination of p-PI3K expression. K562 cells were treated with 140 µg/ml of PC:SA liposome with respect to PC for 90 and 120 min, harvested, lysed and equivalent amount of lysates were separated by SDS-PAGE and electrotransferred. The membranes were probed with anti-phospho-PI3K antibody (top panel). β-Actin was used as loading control (bottom panel).

FIG. 15: Effect of administration of 60 mg of PC:SA liposome with respect to PC on growth of EAC cells ($2 \times 10^6$) (i.p) in Swiss albino mice. Untreated EAC injected mice (A). Mice treated with PC:SA liposome (i.v) on day 2 after EAC injection (B). Mice treated with PC:SA liposome (i.p) on day 2 after EAC injection (C). Animals were sacrificed on day 14.

FIG. 16: To assay the effect of PC:SA and CPT-entrapped PC:SA liposome on the tumor development in syngenic C57BL6 mice (protective and therapeutic aspect). $2 \times 10^6$ B16F10 cells pretreated for 2 h with 140 µg of PC:SA and 7 µg CPT entrapped in 140 µg PC:SA liposomes (with respect to PC) were injected in C57BL6 mice subcutaneously. Animals injected with untreated B16F10 cells were kept as control (protective aspect) (A). B16F10 cells were injected on day 0 and treated on day 2 with either 140 µg of PC:SA liposome alone or with 7 µg of CPT entrapped liposome. Mice injected with B16F10 cells and left untreated served as control (therapeutic aspect) (B). Animals were sacrificed after 21 days and tumor growths were observed.

Figure 17:
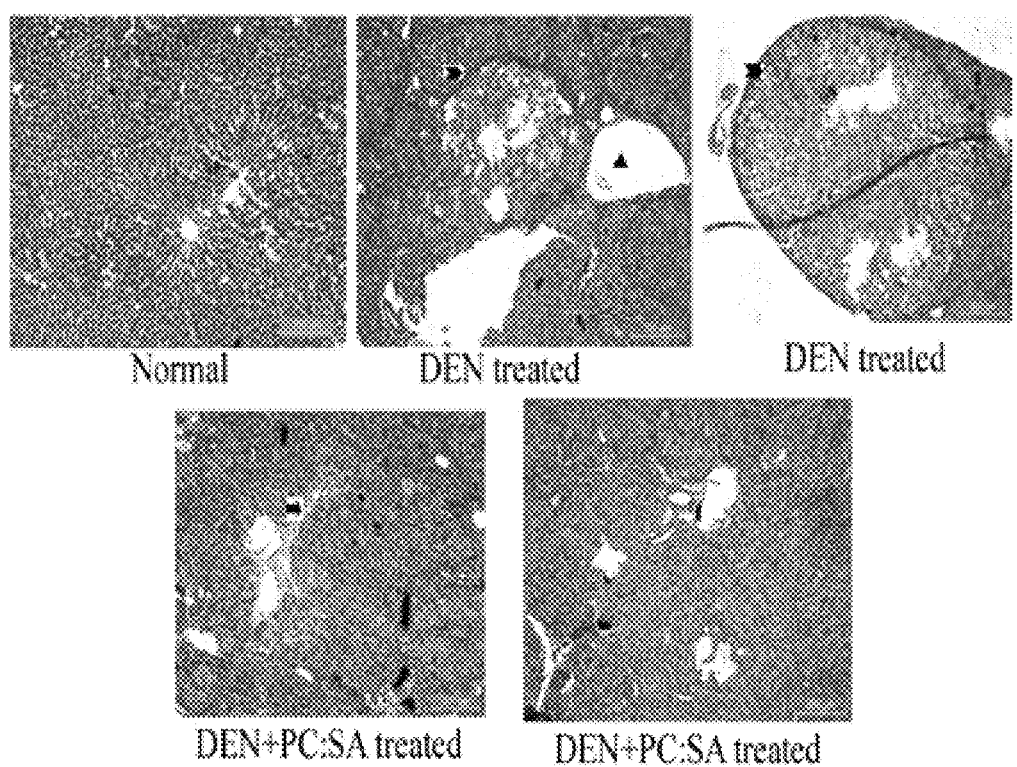

FIG. 17: Histological and histochemical examination of liver sections of experimental rats. Eosin-haematoxylin stained liver sections of control rats showing normal liver architecture, DEN treated control showing (▲) dialated hepatic veins, DEN treated control, showing hyperplastic nodules (▬) and DEN+PC:SA liposome treated, showing architecture similar to normal liver with some amount of periportal fibrosis (➡) Scale Bar: 200 µm.

Figure 18A:
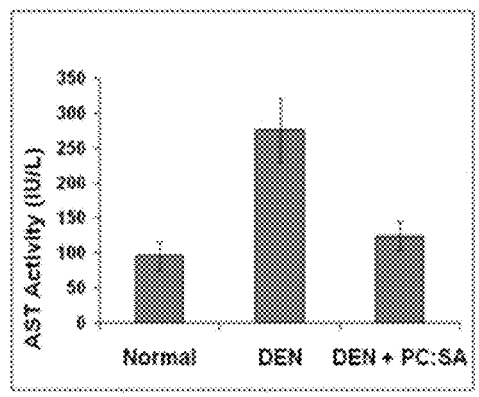
Figure 18B:
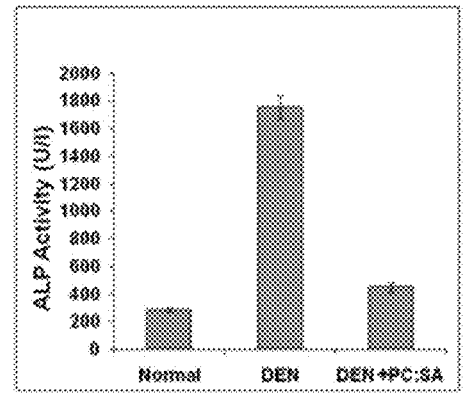
Figure 18C:
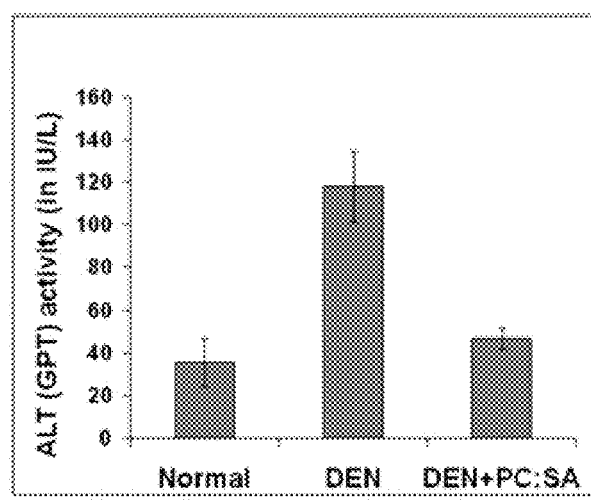

FIG. 18: Effect of PC:SA liposome treatment on serum biochemical parameters in DEN-induced hepatotoxicity in rats. At the end of 18 week starting from the 1st day of DEN administration, blood was collected from heart in the rats of each group. Serum aspartate transaminase (AST), alkaline phosphatase (AP) and serum alanine transaminases (ALT) were determined using a standard kit manufactured by Span Diagnostics Ltd. Values are expressed as mean±SEM.

Figure 19:
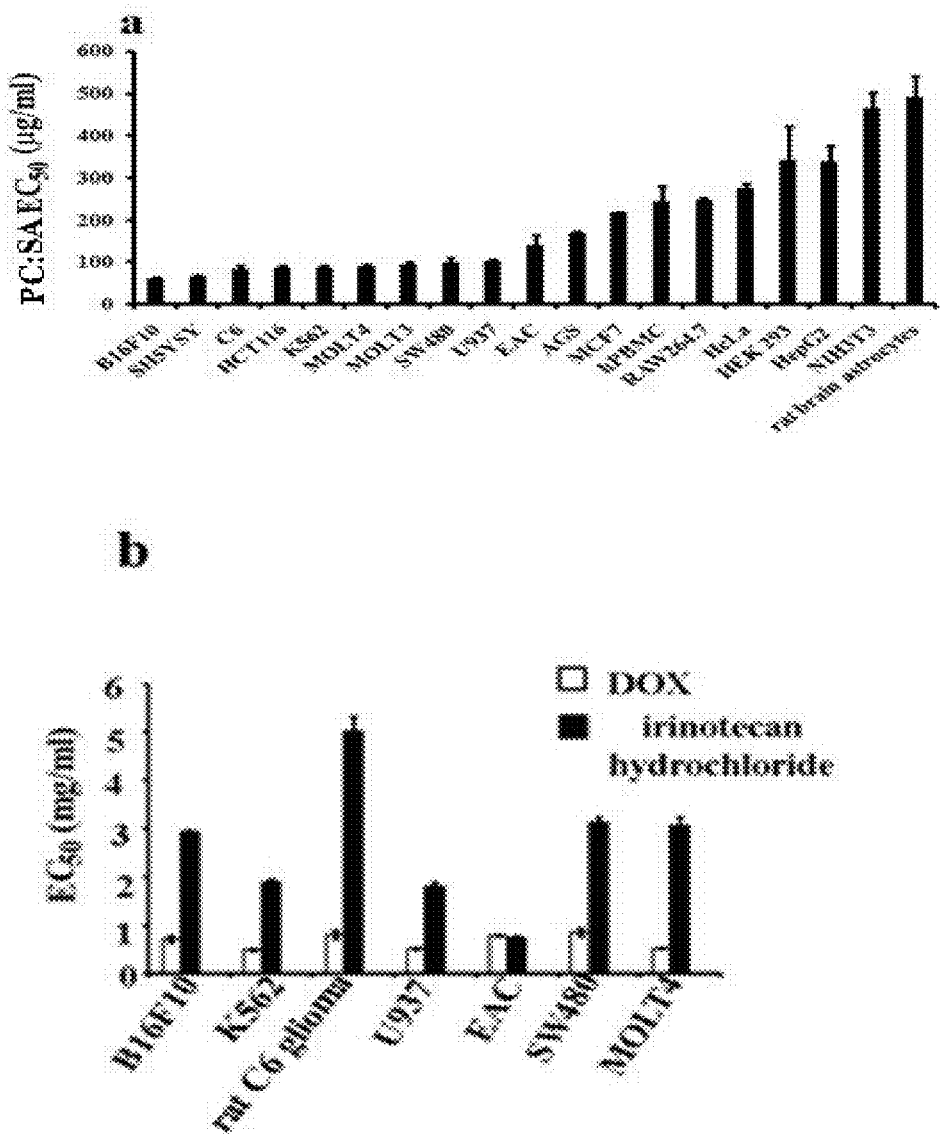

FIG. 19 Comparative study of free PC:SA liposome and free anti-cancer drugs: The $EC_{50}$ values of free PC-Sa liposome (a) and free anti-cancer drugs DOX or irinotecan hydrochloride against cancer cell lines treated for 2 h.

Table 1: Size and Polydispersity index of liposomes.

Table 2: Percentage of CPT entrapped in PC:SA REV, DRV and MLV liposomes.

Table 3: Percentage of DOX entrapped in PC:SA MLV liposome.

Table 4: Effect of single shot injection of 60 mg of PC:SA liposome on EAC cell number and volume of fluid in the peritoneal cavity of Swiss albino mice injected with EAC cells. Values are expressed as mean±SEM.

Table 5: Growth inhibition of B16F10 melanoma by the subcutaneous injections of B16F10 cells pre-treated with 140 μg of PC:SA and 7 μg of CPT entrapped in 140 μg of PC:SA liposomes with respect to PC (protective aspect).

Table 6: Growth inhibition of B16F10 melanoma by the subcutaneous injections of 140 μg/ml of PC:SA and 7 μg of CPT entrapped in 140 μg of PC:SA liposomes with respect to PC in C57BL6 mice previously injected with B16F10 cells (therapeutic aspect). Values are expressed as mean±SEM.

Table 7: Effect of PC:SA liposome on % of increase in RLW in DEN induced hepatocellular carcinoma. At the end of 18 week starting from the 1st day of DEN administration final liver weights of all animals were recorded and RLW were calculated. Values are expressed as mean±SEM.

DETAILED DESCRIPTION OF THE INVENTION

The following abbreviations will be employed:
PC—phosphatidylcholine
SA—stearylamine
PS—phosphatidylserine
Chol—cholesterol
MLV—multilamellar vesicles
DRV—dehydration-rehydration vesicles
REV—reverse phase evaporation vesicle
CPT—camptothecin
DOX—doxorubicin
PBS—Phosphate buffer saline
DDAB—didecyldimethylammonium bromide
DOTAP—[1-(2,3-Dioleoyloxy)]-N,N,N-trimethylamonium propane methylsulfate
PBMC—peripheral blood mononuclear cell
RPMI—Roswell Park Memorial Institute medium
FBS—fetal bovine serum
MTT—3-(4, 5-dimethylthiozol-2-yl)-2, 5-diphenyitetrazolium bromide
FACS—fluorescence-activated cell sorting
PI-propidium iodide
FITC—fluorescein isothiocyanate
Δψ—mitochondrial membrane potential
JC-1—5,5',6,6'-tetrachloro-1,1',3,Y-tetraethylbenzimidazolocarbocyanine Iodide
ROS—reactive oxygen species
H2DCFDA—2',7'-dichlorodihydrofluorescein
DCF—dichlorofluorescein
TEM—Transmission Electron Microscopy
PI3-Kinase—phosphatidylinositol-3-kinase
MAP Kinase—mitogen-activated protein kinase
ERK—extracellular signal-regulated kinases
EAC—Ehrlichs ascites carcinoma
HCC—hepatocellular carcinoma
DEN—diethylnitrosamine
RLW—relative liver weights
H&E—hematoxylin and eosin
AP—alkaline phosphatase
AST—serum aspartate transaminase
ALT—serum alanine transaminases The present disclosure provides liposomal formulation comprising of PC:SA in three forms MLV, DRV and REV in 7:2 molar ratio. In our study we compared the cytotoxic activity of stearylamine-bearing cationic liposome against normal cells (human PBMC, murine macrophage and rat brain astrocytes) and nine different cancer cell lines (three human leukemia, one murine melanoma, two human colorectal adenocarinoma, one rat glioma, and one murine ascites carcinoma cells). We observed that there was a dose-dependent selective killing of these cancer cell lines by PC:SA liposomes and that this killing activity correlated with the exposure of negatively charged phosphatidylserine (PS) on the surface of these cell. PC:SA liposome was non-toxic for normal cells like human PBMC and murine macrophage cell line. Neutral (PC:Chol) and negatively charged (PC:PS) liposome was found to be non-toxic for both cancer and normal cells. Another cell line called human liver hepatocellular carcinoma showed very less killing effect by PC:SA liposome which could be due to very less PS exposure on this cell line. To reconfirm the PS-specific affinity of SA-bearing liposome, PC:SA liposome was pre-incubated with liposome composed of PC:PS. Killing activity of PC:SA liposome was inhibited with gradual increase in the dose of PC:PS liposome. Killing activity of liposomes was also inhibited at 2 hr treatment after pre-blocking the cells with annexinV. Investigation to understand the mechanism of PC:SA-induced killing of cancer cell lines revealed that cell death was due to apoptosis. This was determined by the increase in appearance of PS on the external surface of the plasma membrane (binding to annexin V). Dissipation of mitochondrial transmembrane potential (Δψm), a characteristic feature of apoptosis, was observed in cells treated with PC:SA. Our data show that PC:SA liposome enhanced the levels of reactive oxygen species (ROS). To investigate whether caspase has any role in cell death, cells were preincubated with Z-VAD-fmk, a broad spectrum caspase inhibitor, before PC:SA treatment. There was reduction in the killing activity revealing the caspase dependent mode of cell death. Cell cycle analysis reveals that treatment of cancer cells with PC:SA causes appreciable apoptosis of the cells with accumulation of apoptotic nuclei at the sub G0 phase and an arrest of cells at the G2-M phase. Involvement of MAPK mediated apoptotic pathway, phosphatidylinositol-3-kinase (PI3K)/serine/threonine kinase (Akt) signaling pathway and activation of pro-apoptotic protein Bid were observed in the killing activity of PC:SA liposome against the cancer cell lines. A single shot injection of PC:SA liposome inhibits the growth of Ehrlichs ascites carcinoma in Swiss albino mice. The treatment with PC:SA liposome prevented the liver from developing diethylnitrosamine (DEN)-induced hepatocarcinoma in adult male Swiss Albino rats. Treatment with the formulation of B16F10 in syngenic black mice C57BL6J causes preventive and therapeutic effect in animal model. Anti-cancer drugs like CPT and DOX entrapped in PC:SA liposome increases the anti-cancer effect of the free drug and free liposome against the cancer cell lines. Similarly treatment with CPT entrapped PC:SA of B16F10 in syngenic black mice C57BL6J increases the anti-tumor effect of the free liposomein animal model. Others have previously reported that some cationic antibacterial peptides exhibit a broad spectrum of cytotoxic activity against cancer cells, which could provide a new class of anticancer drugs. The anticancer activity of a cationic amphiphilic peptide ABP-CM4, an antibacterial peptide from *Bombyx mori*, against leukemic cell lines THP-1, K562 and U937 was evaluated, and the cytotoxicity compared with the effects on non-cancerous mammalian cells, including peripheral blood mononuclear cells (PBMCs), HEK-293 and erythrocytes (42). Various tumor cells have elevated surface levels of negatively charged phospholipids, i.e. PS. Cytotoxic activity of the NK-lysin derived peptide NK-2 was compared against normal human lymphocytes and seven different cancer cell lines (two neuroblastoma cell lines LA-N-1 and SH-SY5Y, colorectal adenocarcinoma cancer cells SW480, lymphoma cell line U937, leukemia cell line K562 derived from chronic myelogenous leukemia, Jurkat and MOLT-4 both derived from acute lymphoblastic leukemia). NK-2 which consists of 27 amino acid residues with an overall positive net charge and adopts an amphipathic, alpha-helical secondary structure upon membrane interaction. It was demonstrated that NK-2 selectively kills some cancer cells and that this killing activity correlates with the membrane exposure of negatively charge PS on the surface of these cells and the capacity of the peptide to intercalate into PS-containing model membranes (10). Patients with cancer are at increased risk for thrombotic complications. B16F10 and WM-266-4 melanoma cells expose PS on their surfaces. The presence of PS is essential for the assembly of coagulation complexes leading to robust thrombin formation (17). Rat C6 glioma cells support all procoagulant reactions leading to robust thrombin formation. This ability results from concomitant tissue factor (TF) exposure and from the presence of anionic lipid PS at the outer leaflet of cell membrane (18). In the present study, we report that SA-bearing cationic liposomes in 7:2 molar ratio have dose-dependent anti-tumor efficacy as proved by its effect on B16F10 murine melanoma cells, K562, U937, MOLT4, rat C6 glioma, SW480, HCT116 and Ehrlichs ascites carcinoma cells by interacting with the negatively charged PS on the surface of the cancer cells. Two types of liposomes neutral (PC:Chol) and cationic (PC:SA) were prepared by three different methods (MLV, DRV and REV). We took two cell lines: B16F10 murine melanoma which expresses considerable amount of PS on its surface and non-cancerous cell line RAW 264.7 murine macrophage. The latter, thus serves as our control cells. In case of K562, MOLT4 and U937 normal PBMC serves as the control cells and in case of rat C6 glioma cell line rat brain astrocytes serve as control. PC:SA liposome also showed anti-tumor activity against two humancolorectal cancer cell lines SW480 and HCT116. The neutral PC:Chol liposomes did not show significant cytotoxicity on cancer cells whereas the cationic PC:SA ones proved to be very effective in killing these cells. Next, we checked if the cationic liposomes could prove to be equally effective in killing RAW 264.7, normal human PBMC and cancerous cell line HepG2. However, they exhibited much lesser cytotoxicity on these cells which can be attributed to their low surface PS content. Thus it was found that empty cationic liposomes had intrinsic killing ability on the cancer cells. It has been seen in previous studies with *Leishmania* parasites that PC:SA liposomes involves specific interaction with negatively charged PS of parasite membrane, resulting in severe damage of the membrane and ultimate death of the parasite (22). Similar mechanism of action of these liposomes might be responsible for killing of the cancer cells in our study which is a part of our future plan of work. We wanted to determine the role of SA in PC:SA in the killing response against cancer cell lines. We blocked the cationic PC:SA liposome with anionic PC:PS liposome. The PS of PC:PS liposome blocks the SA of PC:SA liposome. After preblocking, the liposome was used to treat to different tumor cell lines (K562, U937 and rat C6 glioma). MTT results indicate that pre-blocking PC:SA liposome (120 µg/ml) in increasing doses of PC:PS (7:2) liposome effectively decreases the killing efficacy of the liposome, indicating the role of SA in the killing effect of PC:SA liposome. It is hypothesized that SA of PC:SA liposome binds with the PS on the surface of the tumor cells and causes the killing effect. To confirm the PS-specific affinity of SA-bearing liposome, we showed that killing activity of liposomes was also inhibited at 2 hr treatment after pre-blocking the cancer cells (K562 and B16F10) with annexin V.

Apoptosis is by far the best characterized type of cell death and classified as programmed cell death 1. It is defined by morphological features (rounding up of the cell, reduction of cellular and nuclear volume, nuclear fragmentation, plasma membrane blebbing and phosphatidylserine exposure, loss of mitochondrial membrane potential, generation of reactive oxygen species (ROS) and caspase activation (43). On treatment with 140 µg/ml of PC:SA liposome, cancer cell lines like K562, U937 and MOLT4 showed a significant increase in the population of the early apoptotic cells indicated by annexin V positive cells. A small number of cells showed annexin V and PI positive indicating late apoptotic cells too. Normal human PBMC cells exhibited a small increase in the percentage of early apoptotic cells on treatment with 140 µg/ml of PC:SA MLV. Hence, PC:SA shows selectivity for normal and cancer cells ensuring safety and effectivity. Analysis of mitochondrial membrane potential ($\Delta\psi$) by JC1 staining showed that the untreated control cells had a polarized $\Delta\psi$ (non-apoptotic, healthy cells). Dissipation of mitochondrial transmembrane potential ($\Delta\psi m$), a characteristic feature of apoptosis, was observed in K562 cells treated with 140 µg/ml of PC:SA. There was a loss in $\Delta\psi$ on treatment of B16F10 cell line with 7 µg/ml of CPT indicative of apoptosis. However, there was a sharp increase in the $\Delta\psi$ depolarization on addition of 140 µg/ml of PC:SA MLV on B16F10 cell line. This significant increase strengthens our findings that empty cationic PC:SA MLV liposomes are effective apoptotic agents against cancer cells. The depolarization further increased with the treatment of CPT entrapped PC:SA MLV liposomes. This showed that the drug entrapped liposomes had a synergistic effect in lowering the $\Delta\psi$ compared to CPT or liposomes alone. PC:SA liposome also increases the level of reactive oxygen species (ROS) in cancer cells. Cell cycle analysis reveals that treatment of B16F10 and K562 cells with PC:SA causes appreciable apoptosis of the cells with accumulation of cells at the sub G0 phase. Whereas, in case of U937 there is an arrest of cells at the G2-M phase as well as accumulation of apoptotic nuclei at the sub G0 phase and in MOLT4, there is an appreciable arrest of cells at the G2-M phase. There is no effect as such on PBMC and RAW 264.7 cells.

To determine the molecular mechanism of the action of PC:SA liposome the K562 cells were pretreated with pan-caspase inhibitor Z-VAD-fmk prior to liposome treatment the killing efficacy of the liposome effectively decreased. This indicates that the anti tumor efficacy or apoptosis inducing PC:SA liposome may be induced via a caspase mediated pathway.

Activation of extracellular signal-regulated kinases (ERK) stimulates downstream signaling cascades and also modifies transcription causing apoptotic changes. Caspase 9 when cleaved gets activated and form part of the apoptosome complex and activate caspase 3 downstream which is also cleaved by PC:SA treatment. In our experiments we have observed the effect of PI3K signaling kinase. Involvement and activation of ERK indicates MAPK mediated apoptotic pathway and downregulation of p-PI3K indicates phosphatidylinositol-3-kinase (PI3K)/serine/threonine kinase (Akt) signaling pathway. Involvement of p21 and other cell cycle proteins indicates the hindrance of cell-cycle pathway as a probable mechanism for PC:SA mediated anticancer effect in some cell types. Our results demonstrate that pro-apoptotic protein Bid is essential for induction of apoptosis of cancer cells by PC:SA liposome.

When CPT is entrapped in PC:SA liposome in the molar ratio 7(PC):2(SA):0.7(CPT) it increased the anti-cancer effect of the free liposome and free CPT against B16F10, EAC, C6 glioma, SW480 and U937 cell lines. In contrast PC:SA-CPT showed very less effect on human PBMC of healthy donor. The treatment with the formulation (350 µg/kg body weight of CPT entrapped in 7 mg/kg body weight of PC:SA liposome with respect to PC) of B16F10 in syngenic black mice C57BL6J increases the anti-tumor effect of the free liposome in animal model.

When DOX is entrapped in PC:SA liposome in the molar ratio 7(PC):2(SA):0.7(DOX) it increased the anti-cancer effect of the free liposome and free DOX against C6 glioma, EAC and U937 cell lines.

In 1932, Loewenthal and Jahn (1932) obtained the liquid form in the peritoneum of the mouse and named it as "Ehrlich ascites carcinoma" due to the ascites liquid. Together with the carcinoma cells Ehrlich ascites carcinoma (EAC) has a resemblance with human tumors which are the most sensitive to chemotherapy due to the fact that it is undifferentiated and that it has a rapid growth rate (44). The mouse Ehrlich ascites tumor (EAT) cell also has a negatively charged surface with a measured isoelectric point of about pH 4.0. It seemed possible that sialic acid might be responsible for the negative charge of the EAT cell (45). In the present study the potential anti-cancer effects of single shot injection (i.v and i.p) of 1.7 g/kg body weight i.e 60 mg of free PC:SA liposome with respect to PC was tested. The in vivo inhibition of tumour cells growth by PC:SA liposome might be due to its preferential binding with the negative charges on the tumour cell surface.

Hepatocellular carcinoma (HCC) is one of the most common malignant tumors worldwide and the prognosis still remains dismal (46). Angiogenesis plays a significant role in the aggressiveness of FICC. The only potential curative modality for HCC is surgery, including transplantation, yet the recurrence rate for this particular cancer is high and long-term survival rate is rather poor. Both conventional chemotherapy and radiotherapy have been found to be ineffective or only minimally effective in patients with unresectable HCC (41). 3 doses (i.v) of 800 mg/kg body weight i.e 80 mg of PC:SA liposome has proved to be effective in protecting the rat liver from diethylnitrosamine (DEN) induced altered hepatic functioning, prevented DEN induced hyperplastic nodule formation. Our studies have shown distorted histopathological changes in the liver with formation of hyperplastic nodules and atypical nuclei on DEN administration which are indications of DEN induced hepatocarcinogenesis. Remarkable pathological improvement was noticed in rats treated with PC:SA liposome.

Through the present work we propose that PS on cancer cells can be utilized effectively as a target for liposomes containing cationic lipids. This unique mode of selection render the SA bearing liposomes valuable drug delivery systems as they are biocompatible and can be administered via various routes. The anticancer drugs entrapped in these liposomes are more stable as they are protected from early degradation due to interaction with the biological environment. The side effects of the drugs are also reduced thus improving their therapeutic efficacy.

EXAMPLES

The following examples are given by way of illustration of the present disclosure and therefore should not be construed to limit the scope of the presentdisclosure.

Example 1

Preparation of PC:Chol and PC:SA Liposomes

Preparation of Liposomes Multilamellar Vesicles (MLV)

Liposomes were prepared with PC (20 mg) in association with SA (2 mg) or. Chol (3 mg) (Fluka, Switzerland) at a molar ratio of 7:2. In brief, liposomes were prepared by adding lipids in chloroform, followed by evaporating the organic solvents to form a thin film in a round-bottom flask. The film was dried overnight in a vacuum dessicator. The film was rehydrated in 1 ml of 20 mM PBS (pH 7.4), and the suspension was sonicated for 60 s in an ultrasonicator, followed by incubation for 2 h at 4° C. before using. The concentration of stock solution of the liposomes formed was 20 mg/ml with respect to PC. (22).

Reverse-Phase Evaporation Vesicles (REV):

Liposomes were prepared with PC (20 mg) in association with SA (2 mg) or with Chol (3 mg) (Fluka, Switzerland) at a molar ratio of 7:2, and were dissolved in ether:chloroform:methanol (9:4.2:1 v/v/v) in a round bottomed flask. The film was kept overnight for desiccation in vacuum dessicator. The film was rehydrated with 1 ml PBS and is purged with nitrogen. The mixture was sonicated to bath sonication at 4° C. for 5 min. Organic solvents were removed by rotary evaporation at 30° C. for 30 min.

The flask was again purged with nitrogen and then kept for incubation in water bath at 45° C. for 30 min. The liposome was then stored at 4° C. The concentration of stock solution of the liposomes formed was 20 mg/ml with respect to PC (23).

Dehydration Rehydration Vesicles (DRV):

The lipid mixtures of identical molar ratio detailed above were dissolved in chloroform ina round bottomed flask followed by evaporation of the solvent to form a thin film. The film was kept overnight in a vacuum desiccator for desiccation. Rehydration of the film was carried out with 1 ml of sterile distilled water after which it was vortexed and the resulting suspension was sonicated in a bath sonication at 4° C. for 10 min (at 1 min intervals). It was then allowed to stand for 2-3 h. The mixture was then freeze dried and the powdered mixture was rehydrated with 0.02M PBS (pH 7.4) in a stepwise manner. Volume of PBS equivalent to one-tenth of the original volume of liposome was added followed by a 30 min interval. This step was repeated twice. Finally, the mixture was resuspended properly and PBS was added to make up the original volume. The liposome was stored at 4° C. for 2 h before using, (23).

Measurement of Vesicle Size of Liposomes

The diameter of the liposomes and the polydispersity index were determined by Photon Correlation Spectroscopy (PCS) on Nano Zs Zetasizer (Malvern Instruments, Worcestershire, UK) by diluting 1 µl of liposome to 50 µl doubly filtered (0.22 µm pore size) distilled water. Polydispersity index of 0.0 represents a homogenous particle population whereas 1.0 indicates a heterogeneous size distribution in the liposome preparations.

Preparation of PC:SA Liposomes Entrapped with CPT

CPT encapsulated REV, DRV and MLV liposomes were prepared by adding DMSO and methanolic solution of 1 mg/ml CPT to the lipids in the respective organic solvent followed by formation of a thin film. The liposomes were processed further as mentioned earlier. The unencapsulated drug was separated from the liposome by two successive washings in PBS by ultracentrifugation (100,000 g, 30 min, 4° C.). The percentage of CPT incorporated in the liposomes was measured spectrophotometrically at 375 nm after dissolving an aliquot of liposomal preparation in methanol. Finally, the liposomes were stored at 4° C. (29).

Preparation of PC:SA Liposomes Entrapped with DOX

DOX was entrapped in MLV PC:SA liposomes. Briefly, the lipid film prepared with PC and cationic lipid SA at a molar ratio of 7:2 was hydrated with 20 mM phosphate-buffered saline (PBS) containing 1 mg/ml of DOX and sonicated for 60 s. Unentrapped drug was washed with PBS through ultracentrifugation at 1,00,000×g for 45 min. PC:SA with entrapped DOX was finally resuspended in PBS. For estimation of DOX entrapment efficacy, the liposome was dissolved in 10% Triton-x and measured by Uv-vis spectrophotometry at wavelength of 480 nm. The loading or entrapment efficiency is given by the formula: Entrapment efficiency (%)=(Encapsulated drug in liposomes/Amount of total drug)×100% (48). The concentration of stock solution of all the liposomes formed was 20 mg/ml with respect to PC.

The size and Polydispersity index of PC:SA REV, DRV and MLV liposomes were obtained by Dynamic Light Scattering as shown in Table1. Thus, in our studies REV was smaller in size compared to DRV and MLV. The Polydispersity index indicates the presence of a heterogeneous population in the liposomes prepared by all the three methods.

In our experiment MLV showed maximum CPT entrapment of 100% followed by DRV (88%) and REV (56%) (Table 2). The result shows that the percentage of entrapment was highest in MLV form of PC:SA liposome and hence we proceeded to do most of the experiments in the particular form of PC:SA liposome. Entrapment efficacy of DOX in MLV PC:SA liposome was 100% (Table 3).

TABLE 1

| Liposome | Diameter (nm) | Polydispersity Index |
| --- | --- | --- |
| PC:SA REV | 105.7 ± 2.89 | 1 |
| PC:SA DRV | 235.6 ± 2.28 | 1 |
| PC:SA MLV | 202.3 ± 2.94 | 0.884 |

TABLE 2

| Liposome | Percentage of CPT entrapped |
| --- | --- |
| PC:SA REV | 56% |
| PC:SA DRV | 88% |
| PC:SA MLV | 100% |

TABLE 3

| Liposome | Percentage of DOX entrapped |
| --- | --- |
| PC:SA MLV | 100% |

Example 2

Comparison of In Vitro Cytotoxic Effect of PC:Chol and PC:SA (MLV, DRV and REV) and PC:PS Liposomes on Different Cell Lines Murine melanoma cell line B16F10, colorectal adenocarcinoma SW480 cell line, human colon carcinoma HCT116 cell line, rat brain astrocytes and rat C6 glioma cell lines were maintained in Dulbecco Modified Eagle Medium (DMEM) supplemented with 10% fetal bovine serum, sodium pyruvate, 2 mM L-glutamine, penicillin, and streptomycin. Murine macrophage cell line RAW 264.7, MOLT-4 cell line (derived from human acute lymphoblastic leukemia), human leukemia cell lines K-562 and human lymphoma cell line U-937 were maintained in RPMI 1640 medium supplemented with 10% fetal bovine serum, sodium pyruvate, 2 mM L-glutamine, penicillin, and streptomycin. The cells were incubated at 37° C. in a humidified atmosphere of 5% $CO_2$ in air (10). The Ehrlichs ascites carcinoma cells (EAC) were maintained in vivo in Swiss albino mice, by intraperitoneal (i.p.) transplantation of $2 \times 10^6$ cells/mouse every 15 days. Cells were obtained from the peritoneal fluid after 15 days, washed in 0.2M PBS and resuspended in RPMI medium supplemented with 10% FBS. Cortical glia-enriched cultures were obtained from cerebral cortex of zero day old rats. The tissues were cleaned free of meningeal tissue, minced, and mechanically dissociated by passage through a flame-polished Pasteur pipette. Dissociated cells were seeded in DMEM with 10% FBS, 4500 mg/liter glucose, 100 U/ml penicillin and 0.1 mg/ml streptomycin. For glia-enriched cultures, the cells were seeded at $1 \times 10^7$ in a 75-cm² flask. The cultures were kept in a humidified chamber at 37° C. in a 5% $CO_2$ atmosphere for 0.7 to 14 days, the medium (DMEM with 10% FBS, 4500 mg/liter glucose, 100 U/ml penicillin, and 0.1 mg/ml streptomycin) was changed every 4 days. On the last day, flasks were placed on a shaker platform and shaken at 220 rpm for 6 h at 37° C. to remove the oligodendrocytes and microglia in the cultures. The glia-enriched cultures were then grown to confluence before use (31).

For isolation of human peripheral blood mononuclear cells from healthy donors (PBMC) heparinized human peripheral blood was obtained from healthy donors and the mononuclear cells (PBMC) were isolated by the density sedimentation on Histopaque-1077 (400×g, 30 min at RT) and washed and resuspended in RPMI 1640 supplemented with 10% FCS, 2 mM Lglutamine, penicillin (100 U/ml), and streptomycin (100 mg/ml) (30). For cell proliferation assay freshly harvested cells (at a density of $5 \times 10^5$ cells/ml) were seeded in a 96 well cell culture plate, and cells untreated or treated with different concentrations of PC:SA, PC:Chol and PC:PS liposomes (20-140 μg/ml with respect to PC) and respective time points. Inhibition of 3-(4, 5-dimethylthiozol-2-yl)-2, 5-diphenyltetrazolium bromide (MTT) reduction to insoluble formazan by mitochondrial dehydrogenase was used as a viability parameter for the cells and compared with untreated control. After treatment with drug for 2 or 4 h the cells were washed with 20 mM PBS and incubated with 2 mg/ml MTT solution for 4 h at 37° C. The reduced formazan was solubilised in DMSO and plates were analyzed by determining the $A_{550}$ on Thermo MULTISKAN EX plate reader (22).

Figure 1B:
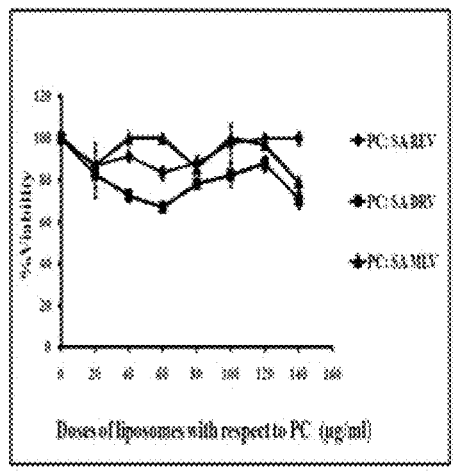
Figure 1C:
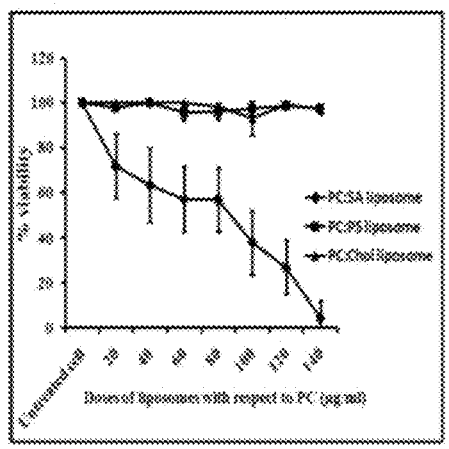
Figure 1D:
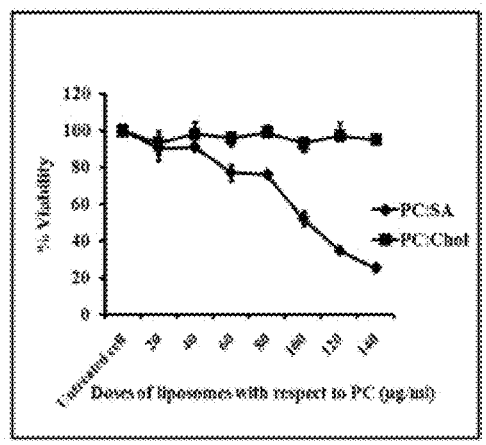

The potency of PC:Chol (neutral) and PC:SA (cationic) liposomes against murine melanoma B16F10 cells were determined by MTT assay. Both the formulations prepared by three different methods i.e. REV, DRV, MLV were used. PC:SA which is a cationic liposome showed considerable amount of killing of B16F10 cells. It showed almost similar killing effect in all its three forms REV, DRV and MLV. The percentage of viable cells at the highest dose of 140 µg/ml after 2 h treatment were 9.162±1.69 for REV, 14.19±1.95 for DRV and 8.075±1.76 for MLV. Conversely, the neutral PC:Chol counterparts did not show any significant killing even at the highest dose of liposome (FIG. 1A). Therefore, PC:SA liposomes exhibited high cytotoxicity as compared with PC:Chol liposomes which are neutral. We examined the effect of these cationic liposomes on murine RAW 264.7 macrophage cells which is a non-cancerous cell line. As evident from the graph, the cationic PC:SA liposomes elicited a much lower killing effect as compared to B16F10 cell line (FIG. 1B).

Figure 1E:
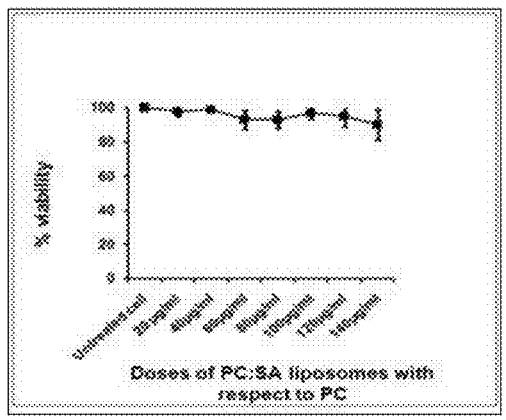
Figure 2A:
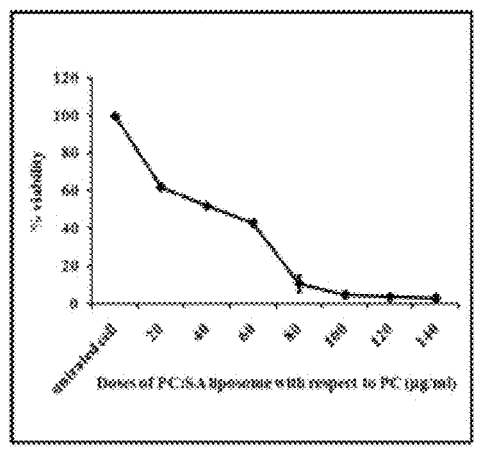
Figure 2B:
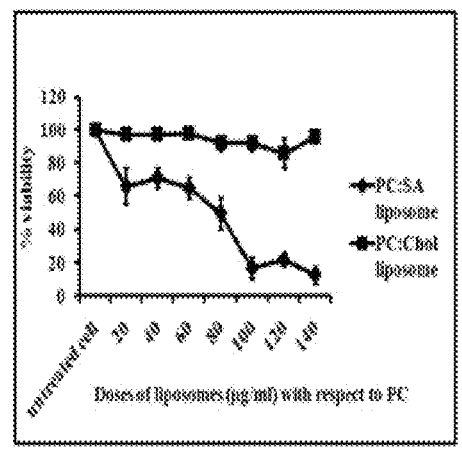
Figure 2C:
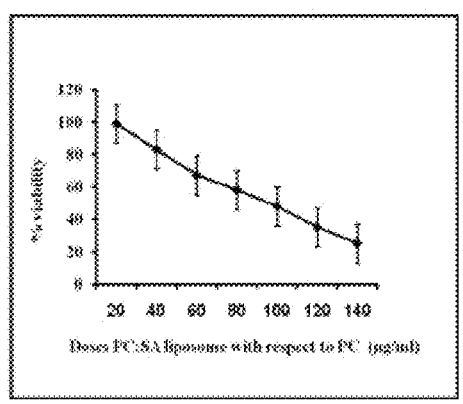
Figure 2D:
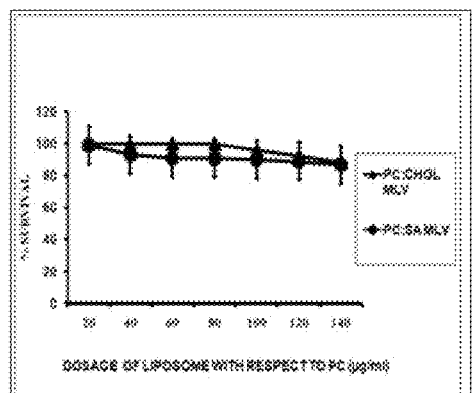

PC:SA MLV cationic liposomes were tested for their ability to kill human leukemia cells lines K562 and U937 by inhibition of MTT reduction. At a dose of 140 µg/ml, the percentage of viable cells was only 4% and 20% for K562 and U937 cells (FIGS. 1C and 1D) respectively after 2 h of treatment. FIGS. 2A and B showed that viability further decreased to 0% and 15% for K562 and U937 cells respectively after 4 h of treatment. When MOLT4 cells were treated with 140 µg/ml of PC:SA liposome with respect to PC for 4 h the percentage of viable cells was 25% (FIG. 2C). In contrast control (human PBMC of healthy donor) (FIGS. 1E and 2D) which was also treated with a similar dose of PC:SA (MLV) liposome and for same durations showed very negligible killing effect. Treatment with PC:Chol (MLV) and PC:PS (MLV) liposomes did not show any killing effect on these cell lines even after treatment with the highest dose of 140 µg/ml (FIGS. 1C, 1D, 2B and 2D).

Figure 1F:
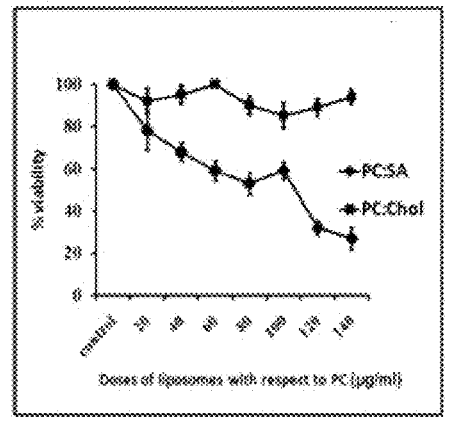
Figure 1G:
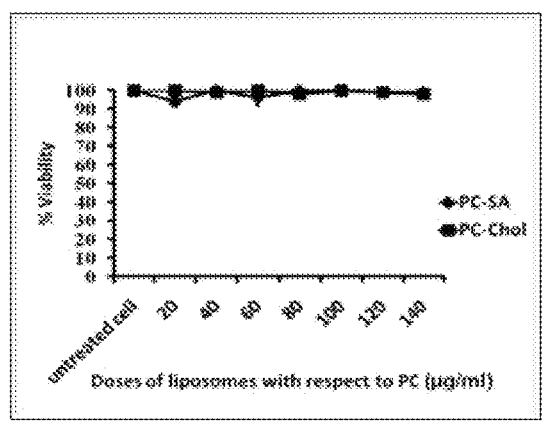
Figure 2E:
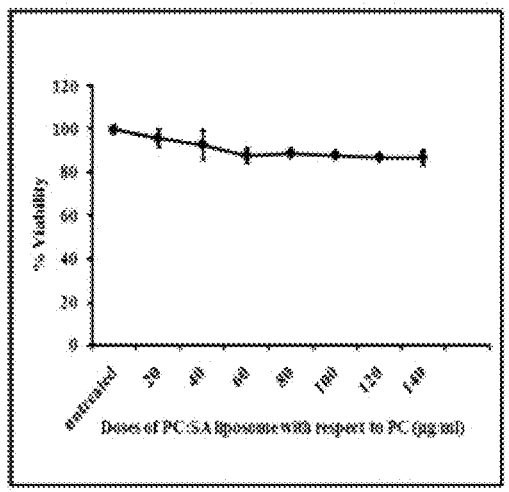
Figure 2F:
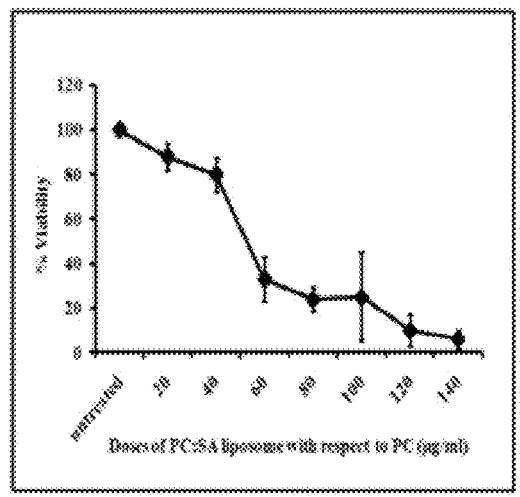

FIGS. 1F and 2F showed that rat C6 glioma cells were susceptible to the MLV form of the cationic liposome with 32% and 6% cells viable at the highest dose of 140 µg/ml after 2 h and 4 h of treatment respectively. FIGS. 1G and 2E showed that PC:SA liposome was non toxic for non-cancerous cells, rat brain astrocytes with 99% and 87% cells viable at the highest dose of 140 µg/ml with respect to PC after 2 h and 4 h of treatment respectively. Treatment with PC:Chol (MLV) liposomes did not show any killing effect on either of these cells even after treatment with the highest dose of 140 µg/ml (FIGS. 1F and 1G).

Figure 1H:
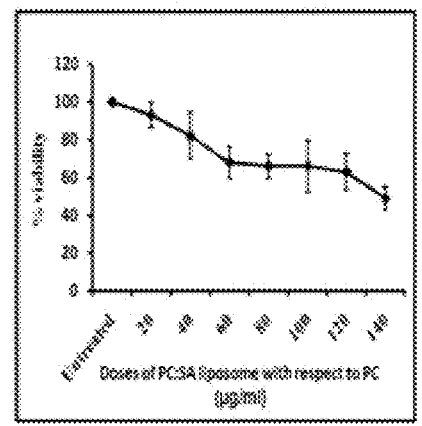
Figure 2G:
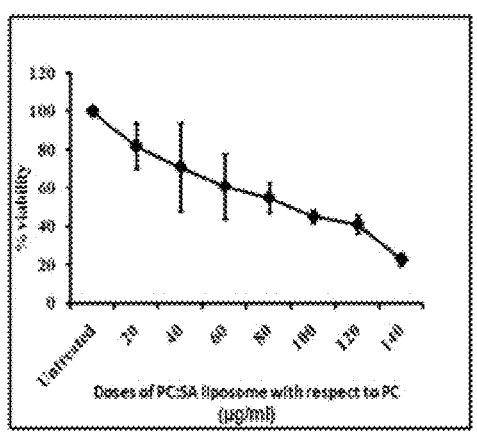

The inhibitory effect of PC:SA (MLV) liposome was also determined by exposure of Ehrlichs ascites carcinoma cells of mouse peritoneal fluid to increasing concentrations of the liposome. The highest concentration of the liposome (140 µg/ml) which reduced cell survival by 67% and 77% in 2 h and 4 h respectively was determined from the cell survivality curve (FIGS. 1H and 2G).

Figure 1I:
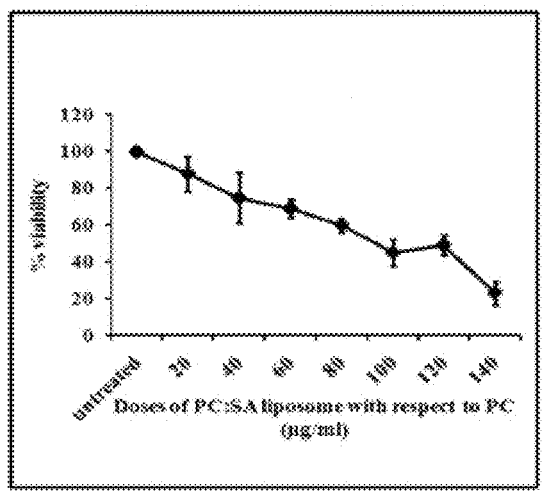
Figure 1J:
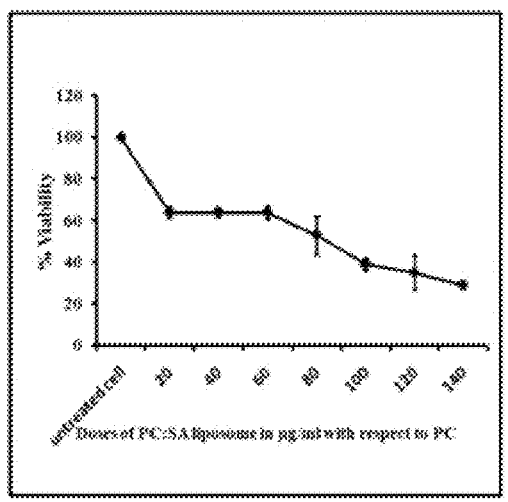

Colorectal adenocarcinoma cells SW480 and human colon carcinoma HCT116 were treated with PC:SA liposome at various concentrations. As seen from FIGS. 1I and 1J exposure to increasing concentrations of PC:SA liposome resulted in a dose-dependent inhibition of the cells.

Figure 1K:
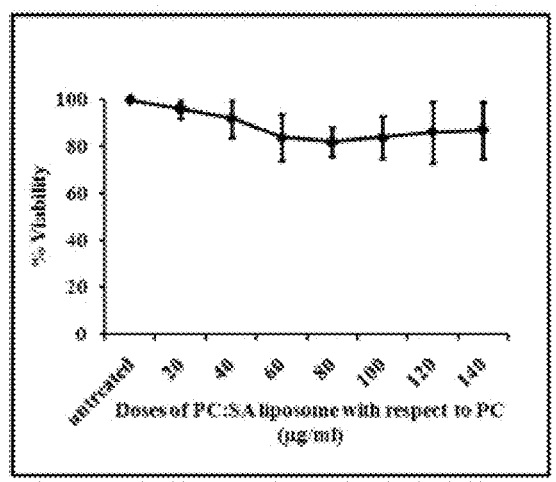
Figure 2H:
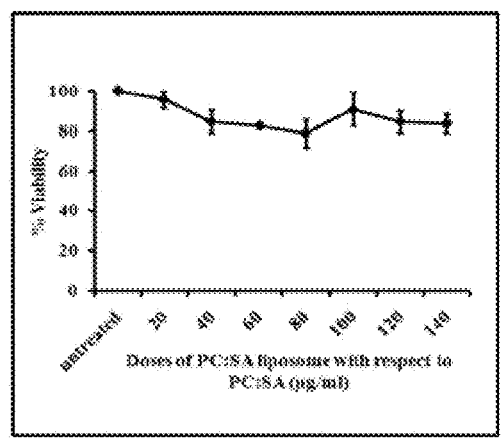

Another cancer cell line called human liver hepatocellular carcinoma HepG2 had very less killing effect showing 87% (FIG. 1K) and 84% (FIG. 2H) viability when treated with graded concentrations of PC:SA liposome for 2 h and 4 h respectively.

Example 3

Figure 3A:
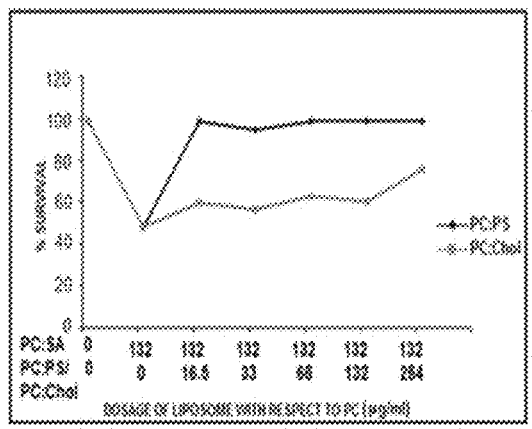
Figure 3B:
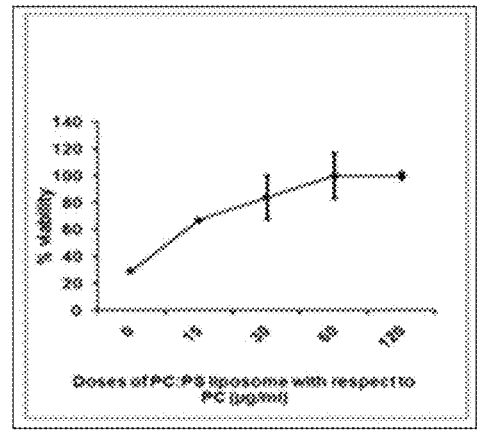
Figure 3C:
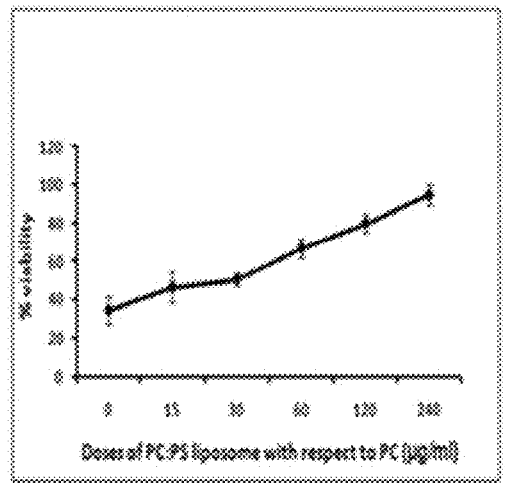
Figure 3D:
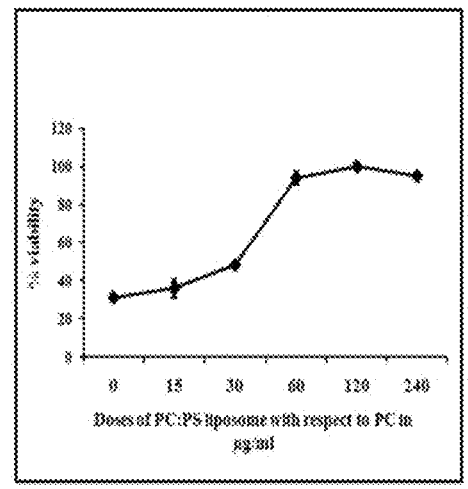

Identification of the Role of Stearylamine in Anti-Tumor Efficacy of PC:SA Liposomes by Observing the Effect of PC:SA (MLV) Liposome on Different Cells after Pre-Blocking the Liposome with PC:PS and PC:Chol Liposomes PC:SA liposomes (120 µg/ml with respect to PC) were incubated for 30 min with different concentrations of PC:PS liposomes (15-240 µg/ml). The cells were treated with the pre-incubated liposomes for 2 hours. Viability of the cells was assayed by MTT reduction (22). FIGS. 3A, 3B, 3C and 3D showed that killing activities of PC:SA liposomes on B16F10, K562, U937 and rat C6 glioma cell lines were inhibited with a gradual increase in the dose of PC:PS liposomes (7:2). Maximum significant inhibition was observed at a concentration of 240 µg/ml of PC:PS. Specificity towards PS was further supported by the negligible effect of the neutral PC:Chol (7:2) liposomes to inhibit the killing potency of the PC:SA liposome. FIG. 3A showed that killing activities of PC:SA liposome on B16F10 cells were unaffected with a gradual increase in PC:Chol liposome (7:2). The result showed appreciable reversal of the effect of PC:SA after with PC:PS liposome but negligible reversal upon pre-blocking with PC:Chol liposome indicating the role of SA in the liposome responsible for PC:SA mediated anticancer effect.

Example 4

Identification of the Role of Phosphatidylserine Expressed on the Surface of Tumor Cells in Anti-Tumor Efficacy of PC:SA Liposomes by Observing the Effect of PC:SA Liposome on Different Cells after Pre-Blocking the Cells with Annexin V for 30 Min To investigate the role of PS in interaction with liposomes, PS was blocked by preincubation of B16F10 and K562 cell lines with annexin V prior to addition of PC:SA liposomes.

Figure 4A:
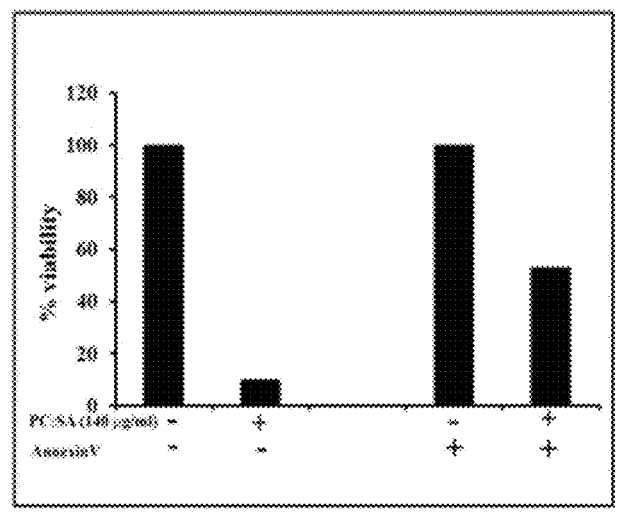
Figure 4B:
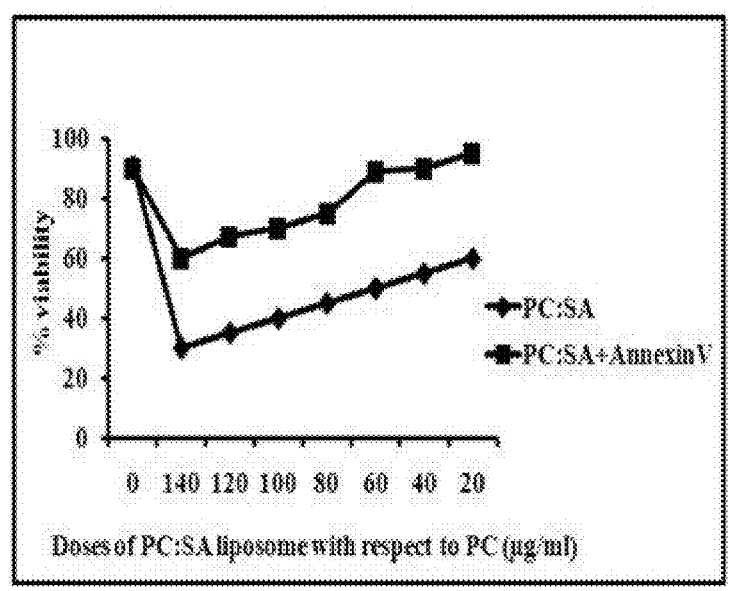

Cell suspensions in binding buffer were incubated with or without annexin V at 37° C. for 30 min. Cells were incubated with PC:SA liposomes (20-140 µg/ml with respect to PC) for 2 h. Viability of the cells was assayed by MTT reduction (22). Capability of PC:SA liposomes (140 µg/ml) to induce 90% on K562 cell line and killing activity at 120 min, was drastically reduced to 50%, through annexin V blocking of surface PS of the cell line indicating significant PS-mediated killing. Non-specific negative-positive charge interaction with other membrane components may be responsible for the remaining 50% killing activity (FIG. 4A). Similar effect was observed in case of B16F10 cell line (FIG. 4B).

Example 5

Effect of Camptothecin Entrapped PC:SA on Different Cell Lines

Figure 5A:
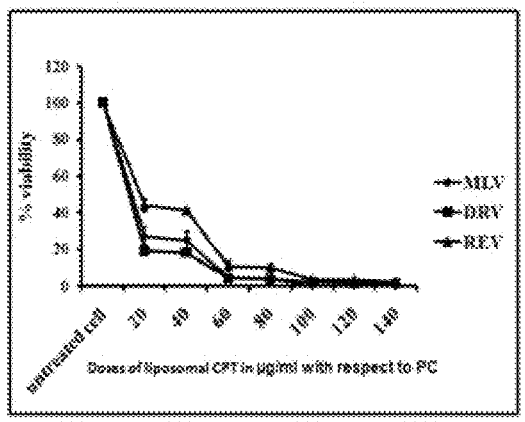
Figure 5B:
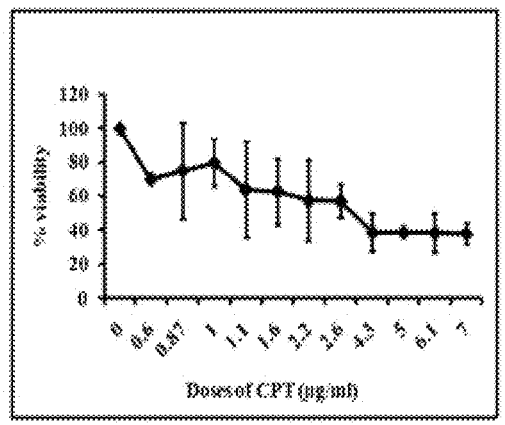
Figure 5C:
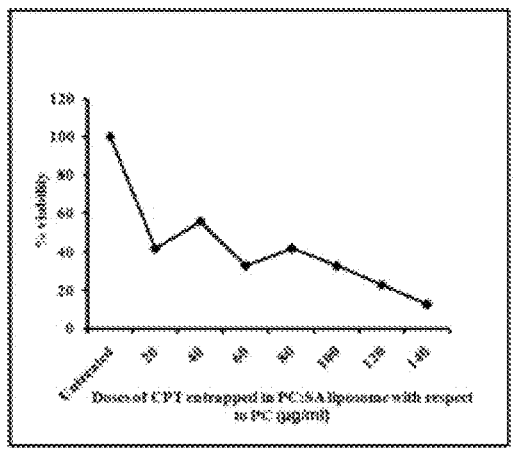
Figure 5D:
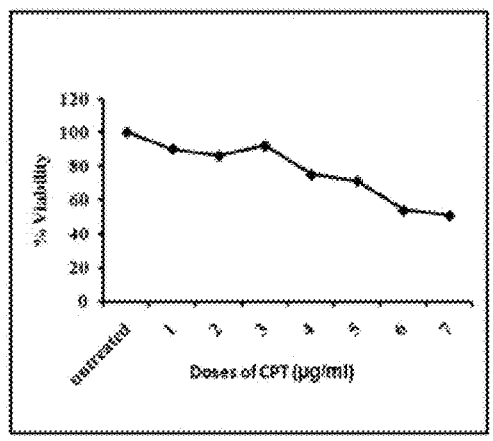
Figure 5:
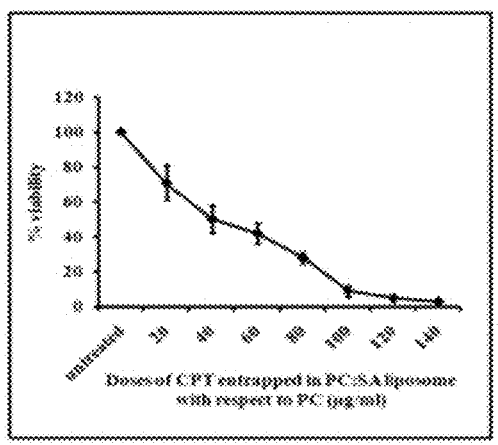
Figure 5:
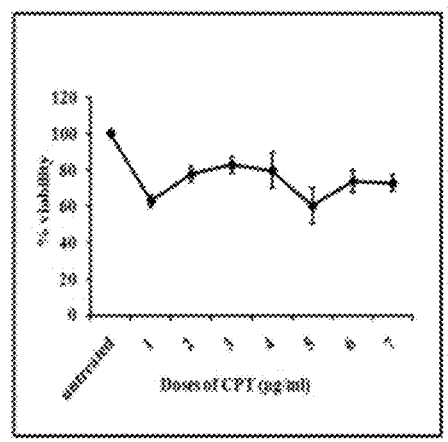
Figure 5G:
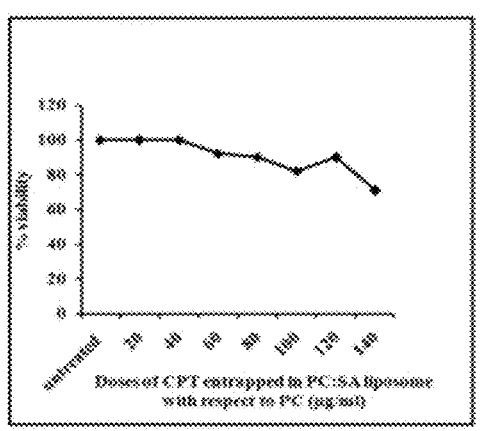
Figure 5H:
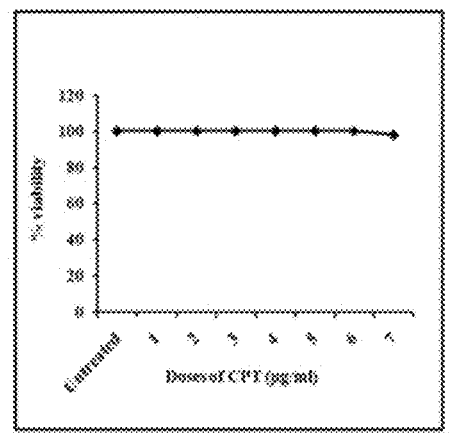
Figure 5I:
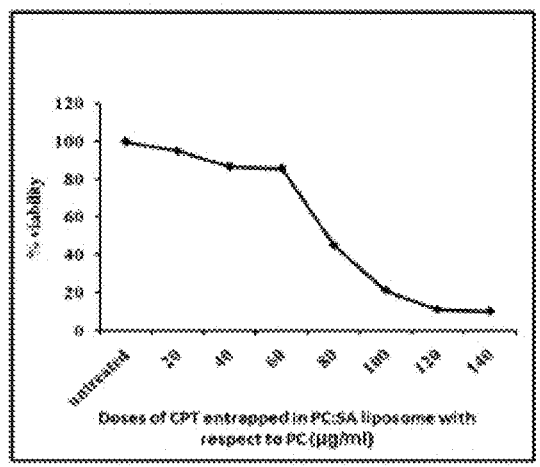
Figure 5J:
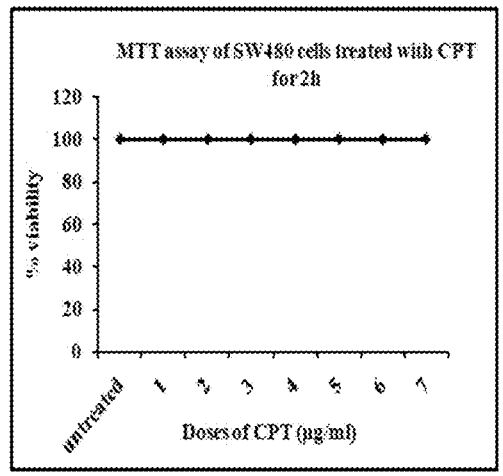
Figure 5K:
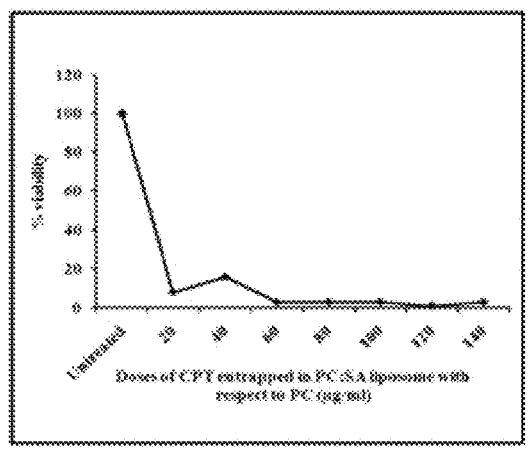
Figure 5L:
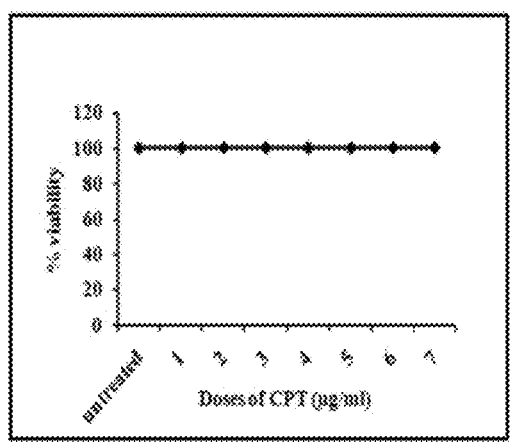

Since PC:SA liposomes showed profound cytotoxicity on different cell lines, we proceeded on to entrap the anticancer drug camptothecin (CPT) in them and compared the cytotoxicity of CPT entrapped in PC:SA REV, DRV and MLV liposomes with equivalent doses of free drug. The molar ratio of the drug entrapped liposome was 7(PC):2(SA):0.7 (CPT). We compared the cytotoxicity of CPT entrapped in PC:SA REV, DRV and MLV liposomes with equivalent doses of free drug on B16F10 cells. FIG. 5B revealed that a dose of 7 µg/ml of free CPT showed 38% viability (FIG. 5B) whereas the same amount of drug entrapped in 140 µg/ml of PC:SA MLV liposome with respect to PC showed about 0% viability (FIG. 5A) after 2 h of treatment. Similarly 2.3% and 1.3% cells were viable with 140 µg/ml of REV and DRV liposomes (drug entrapped) respectively (FIG. 5A) while with the equivalent amounts of free CPT (i.e. 3.9 µg/ml for REV and 6.1 µg/ml for DRV) about 38% of cells survived (FIG. 5B) after 2 h of treatment. Thus, drug entrapped in PC:SA liposomes showed more effective in killing the melanoma cells than corresponding amount of free drug. There was no significant difference in the killing profile of CPT entrapped PC:SA REV, DRV or MLV liposomes. However, PC:SA REV liposome showed slightly lesser cytotoxicity at the lower doses. We wanted to determine the anti tumor efficacy of CPT entrapped PC:SA liposome on EAC, and rat C6 glioma, human PBMC of healthy donor and SW480 cell lines after 2 h of treatment. A dose of 7 µg/ml of free camptothecin entrapped in 140 µg/ml of PC:SA showed effective killing effect on EAC, rat C6 glioma, SW480 and U937 cell lines and with 13% (FIG. 5C), 2% (FIG. 5E), 10% (FIG. 5I) and 3% (FIG. 5J) viability respectively but very less effect was observed on PBMC of healthy donor showing 71% viability at the same dose of liposomal CPT (FIG. 5G). A dose of 7 µg/ml of free CPT showed 56% (FIG. 5D), 71% (FIG. 5F) viability on EAC and C6 glioma cells respectively whereas it showed no killing effect on and normal human PBMC (FIG. 5H). SW480 (FIG. 5J) and U937 (FIG. 5L) cell lines.

The results revealed CPT entrapped in PC:SA liposomes was more effective in killing different cells than corresponding amount of free liposome and drug.

Example 6

Effect of Doxorubicin Entrapped PC:SA on Different Cell Lines

Figure 6A:
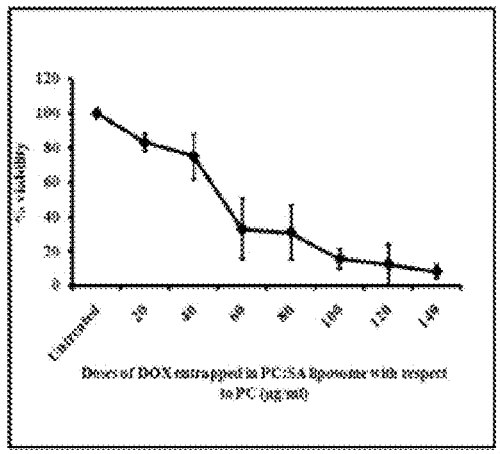
Figure 6B:
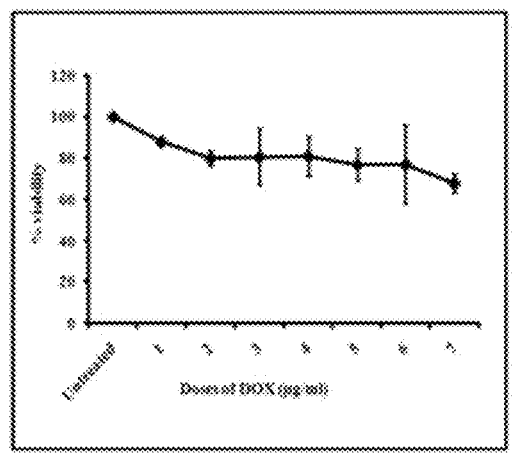
Figure 6C:
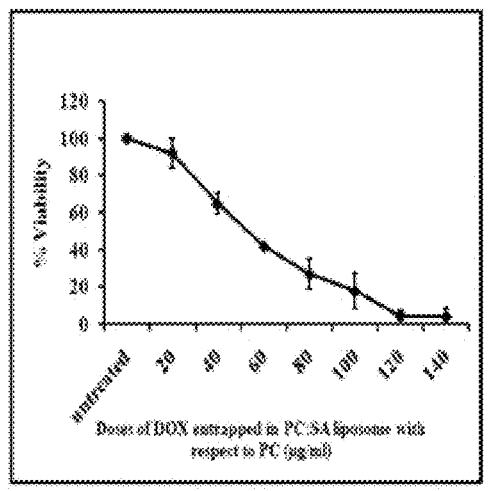
Figure 6D:
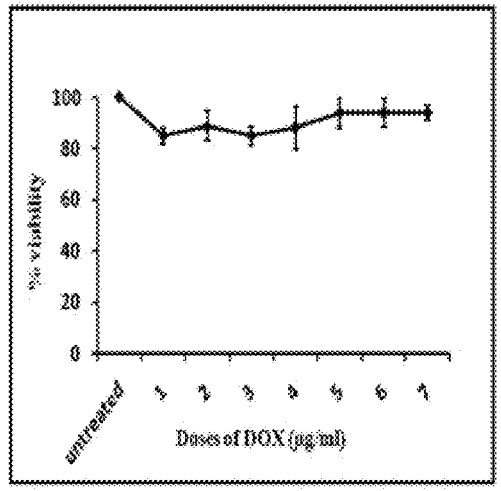
Figure 6E:
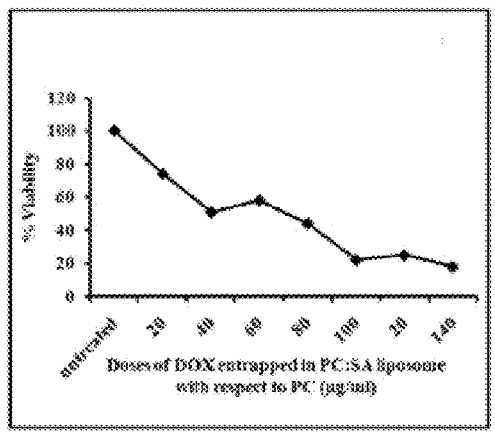
Figure 6F:
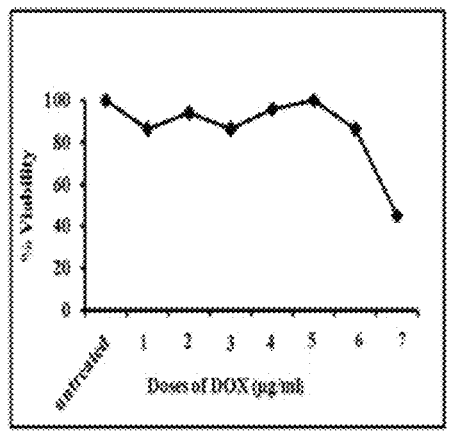

Next we compared the cytotoxicity of DOX entrapped in PC:SA MLV liposomes in the molar ratio 7(PC):2(SA):0.5 (DOX) with equivalent doses of free drug on U937 and rat C6 glioma cell lines. FIGS. 6B, 6D and 6F revealed that a dose of 7 µg/ml of free DOX showed 68%, 93% and 45% viability on U937, rat C6 glioma cell lines and EAC cells respectively whereas the same amount of drug entrapped in 140 µg/ml of PC:SA MLV liposome with respect to PC showed about 8%. 4.3% and 18% viability on U937 (FIG. 6A), rat C6 glioma cell lines (FIG. 6C) and EAC cells (FIG. 6E) respectively after 2 h of treatment. Thus, DOX entrapped in PC:SA liposomes showed more effective killing effect on U937 and rat C6 glioma cell lines than corresponding amount of free drug.

The result indicates a synergistic anticancer efficacy of the PC:SA entrapped drug as compared to free drug or liposome. The synergistic effect ensures low dosage of treatment and decreased chemotherapeutic toxicity of the drug.

Example 7

Flow Cytometric Analysis of PI-Annexin V to Quantify Apoptotic Effect of PC:SA Liposome on Different Cell Lines Detection between the intact viable cells, early apoptotic cells, and late apoptotic or dead cells (necrosis) can be carried out with PI-annexin V double staining. Thus, we performed this assay to explore cell apoptosis. Since the MLV form of PC:SA liposome showed maximum drug entrapment, profound killing effect, and was easy to prepare, we proceeded with it for the further experiments.

Figure 7A:
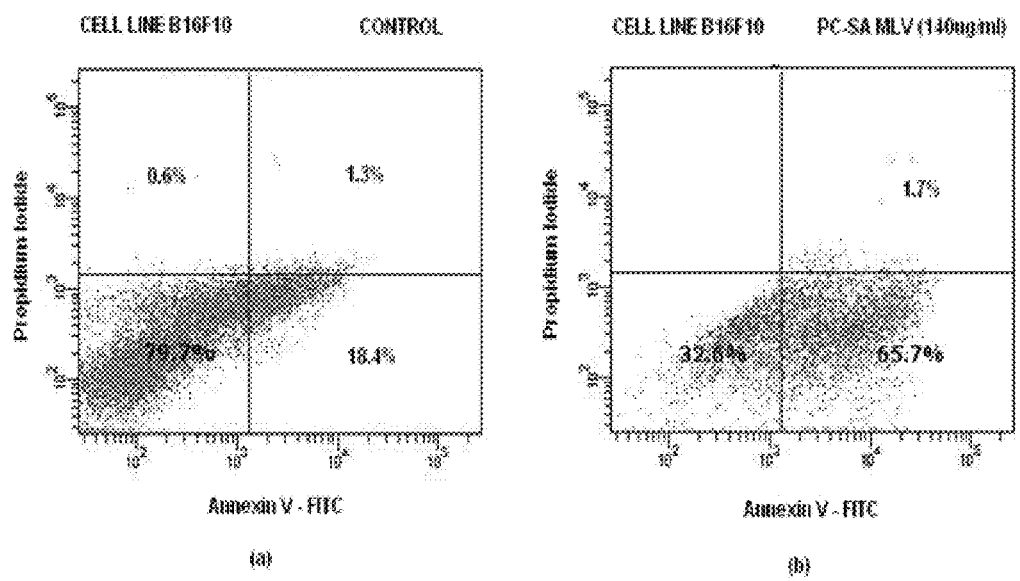
Figure 7B:
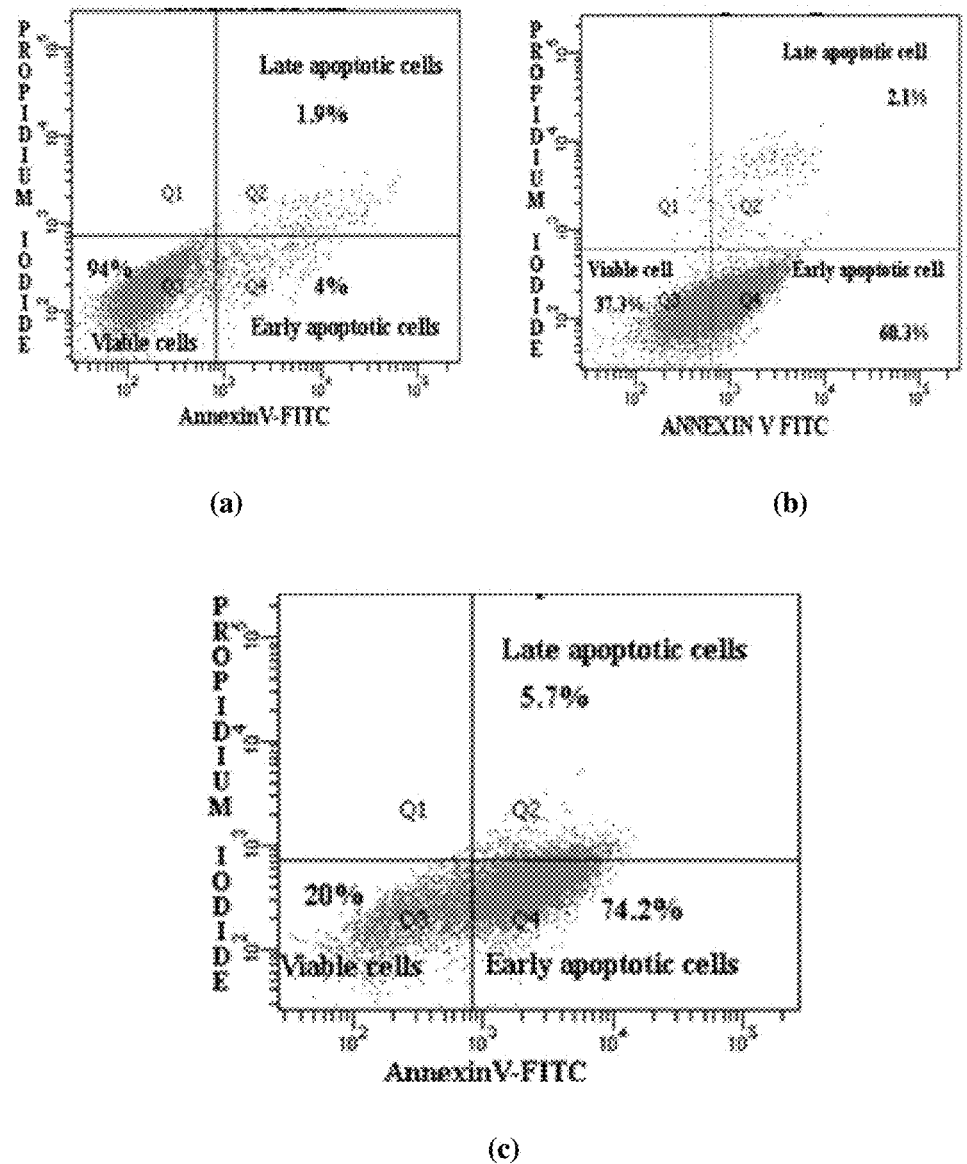
Figure 7C:
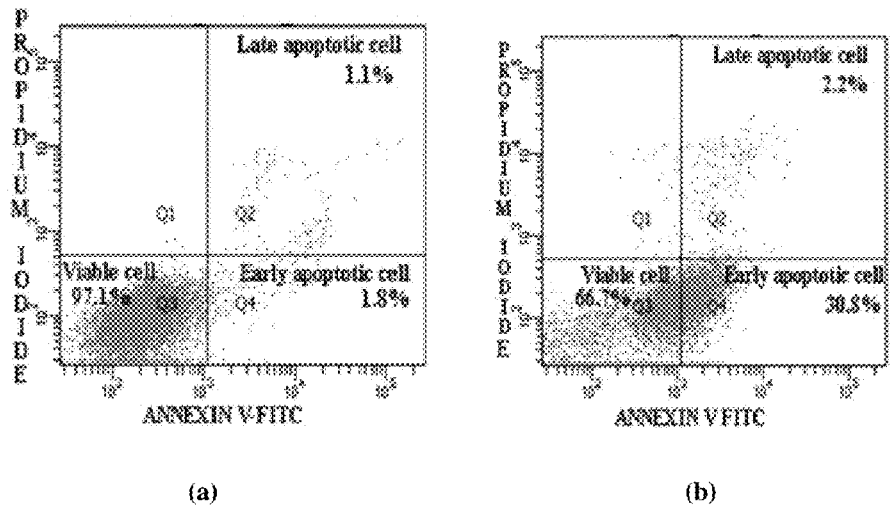
Figure 7D:
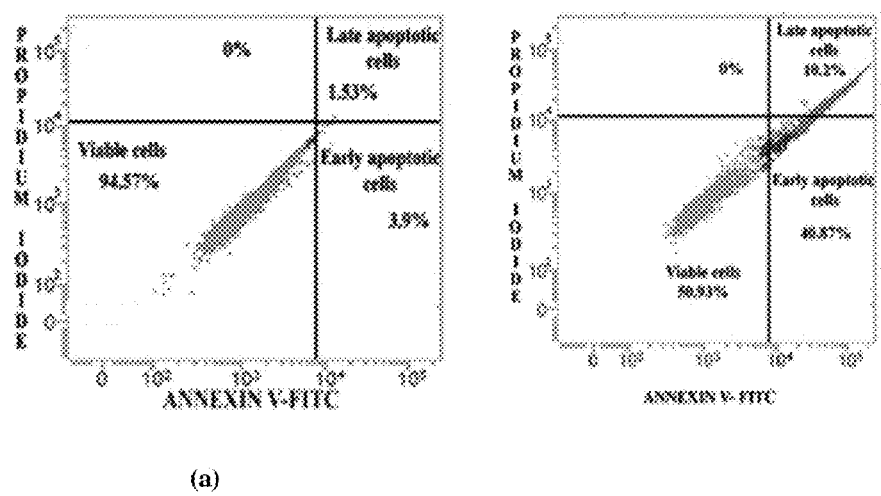
Figure 7E:
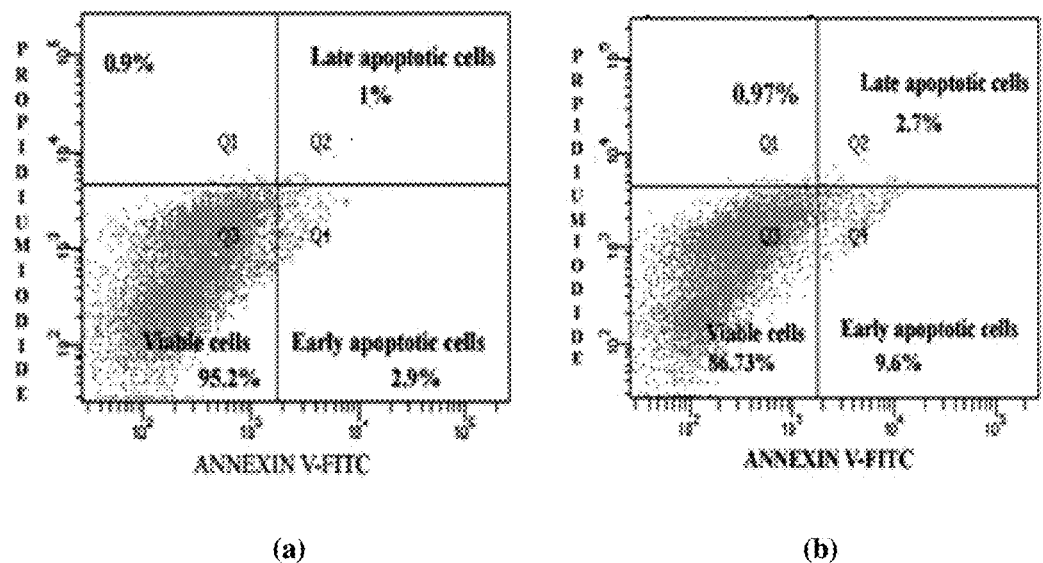

Untreated and liposome treated cell lines ($5 \times 10^5$ cells/ml) were washed and resuspended in annexin V binding buffer (10 mM HEPES, 150 mM NaCl and 2.5 mM $CaCl_2$) at pH 7.3. In order to detect the translocation of phosphatidylserine from inner cell membrane to outer cell membrane (a characteristic feature of cells undergoing apoptosis), cells were subjected to flow cytometric analysis after staining with annexin V-FITC and PI. (FITC annexin V Apoptosis Detection Kit II BD Pharmingen™) (32). For annexin V based apoptosis analysis B16F10, RAW264.7, human PBMC, K562, U937 and MOLT4 cells were analysed after treatment with the highest dose (140 µg/ml) of PC:SA (MLV) liposome with respect to PC. The untreated control B16F10, K562, U937 and MOLT4 human PBMC cells showed about 79.4%, 94%, 97.1%, 94.5% and 95.2% viable cell population (FITC-annexin V and PI negative) respectively. 18.4%, 4%, 1.8%, 3.9% and 2.9% were PS expressing cells (FITC-annexin V positive and PI negative) respectively (FIGS. 7Aa, 7Ba, 7Ca, 7Da, and 7Ea). After treatment, however, a shift in the cell population towards early apoptosis was observed in which there is an increase in FITC-annexin V positive and PI negative cells. The percentage of viable cells for B16F10, K562 and U937 cells now decreased from 79.4%, 94% and 97.1% to about 33%, 37.3% and 66.7% respectively whereas the percentage of cells showing annexin V-FITC positive and PI negative increased from 18.4%. 4% and 1.8% to 66%, 60.3% and 30.8% respectively after treatment for 2 h with 140 µg/ml of PC:SA liposome (FIGS. 7Ab, 7Bb, 7Cb). When K562 and MOLT4 cells were treated with PC:SA liposome for 4 h with 140 µg/ml of PC:SA liposome the percentage of viable cells decreased from 94% and 94.5% to 20% and 50.93% respectively whereas the percentage of cells showing annexin V-FITC positive and PI negative increased to 74.2% and 40.87%. A certain percentage of MOLT4 cells (10.2%) and K562 cells (5.7%) also showed both annexin V-FITC and PI positive indicating late apoptosis (FIGS. 7Db, 7Bc). Thus, on treatment the PS content of the cells increases which indicates that apoptosis is being induced by PC:SA MLV liposome but cell membrane integrity is still maintained. Non-cancerous cells like normal human PBMC were also treated with the same dose and durations with MLV PC:SA liposome. When normal human PBMC were treated with 140 µg/ml of PC:SA liposome for 4 h, percentage of viable cells decreased from 95.2% to 86.7% whereas a small percentage of cells (9.6%) showing annexin V-FITC positive and PI negative (FIG. 7Eb). The results revealed that 140 µg/ml PC:SA (MLV) liposome showed apoptotic mode of killing activity on B16F10, K562, U937 after treatment for 2 h by binding with annexin V-FITC where as K562 and MOLT4 cell line after treatment with 140 µg/ml of PC:SA (MLV) showed both early and late mode of cell death. A very less percentage of PBMCs were found to be apoptotic after treatment with 140 µg/ml of PC:SA liposome.

Example 8

Flow Cytometric Analysis of Reduction in Mitochondrial Membrane Potential ($\Delta \psi$)

The mitochondrial membrane potential is a hallmark for apoptosis. Apoptosis is usually associated with depolarization of mitochondrial membrane potential (Δψ). In non apoptotic cells, JC-1 exists as a monomer in cytosol (green) and accumulates as aggregates in the mitochondria, which appear red. In apoptotic and necrotic cells, JC-1 exists in monomeric form and stains the cytosol green.

Figure 8A:
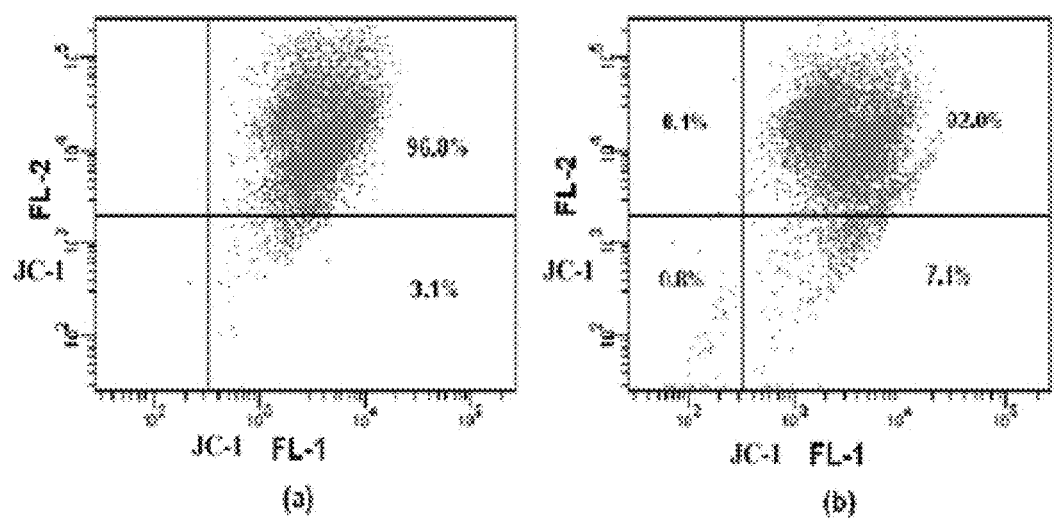
Figure 8B:
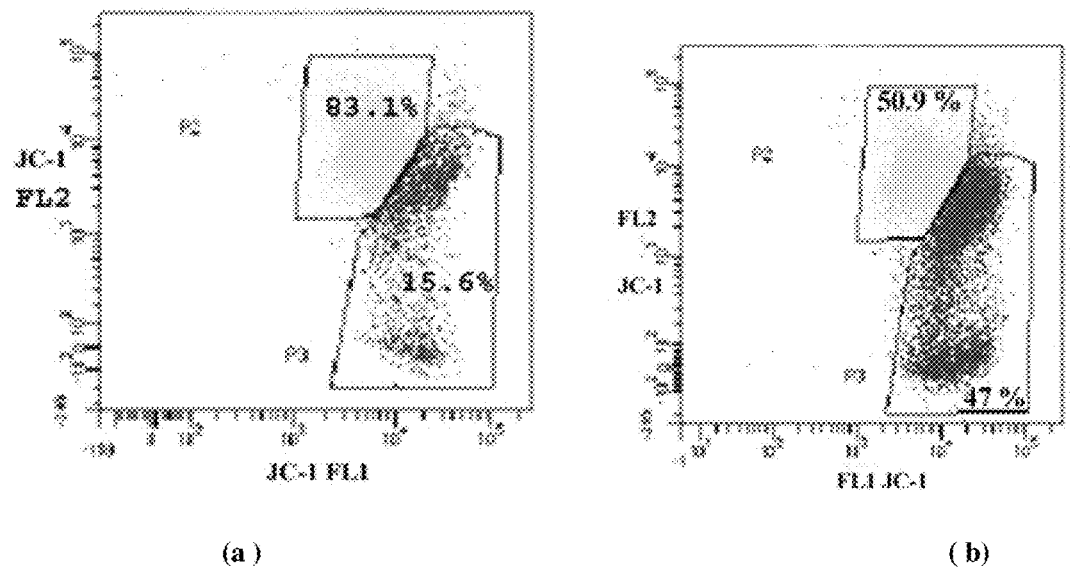

Cells ($5\times10^5$/ml) were treated with PC:SA liposome or CPT entrapped in PC:SA liposome (140 µg/ml with respect to PC) for 2 h and centrifuged at 2000 rpm for 5 min. Supernatant was carefully removed. 0.5 ml of freshly prepared 5,5',6,6'-tetrachloro-1,1',3,Y-tetraethylbenizimidazolocarbocyanine Iodide (JC-1) working solution containing 1:100 JC-1 stain was added to each pellet. The pellets were resuspended. Cells were incubated in JC-1 working solution for 10-15 min at 37° C. in a $CO_2$ incubator. Cells were washed twice following incubation. Cells were then analyzed by flow cytometry. (BD™ MitoScreen Flow Cytometry Mitochondrial Membrane Potential Detection Kit) (33). To detect the changes in Δψ, B16F10 cells were treated with 140 µg/ml PC:SA MLV liposome, 7 µg/ml of CPT entrapped in 140 µg/ml PC-SA MLV liposome and 7 µg/ml of CPT for two hours and analysed by flow cytometry. FIG. 7A shows typical FL-1/FL-2 dot plots for JC-1 staining of B16F10 cell line. Untreated B16F10 cells were Without apoptosis, which have 96.8% red fluorescing J-aggregates and 3.1% green fluorescing monomers (FIG. 8Aa). The increase in green fluorescing monomers 7%, 59% and 73.5% shown in the lower part indicate apoptotic cells due to the treatment for 2 hours with 7 µg/ml of free CPT (FIG. 8Ab), 140 µg/ml PC:SA MLV liposome (FIG. 8Ac) and 7 µg/ml of CPT entrapped in 140 µg/m) PC:SA MLV liposome (FIG. 8Ad) respectively. To detect the changes in Δψ, K562 cells were treated with 140 µg/ml of PC-SA MLV liposome for 2 hrs, and analysed by flow cytometry. FIG. 14 shows typical FL-1/FL-2 dot plots for JC-1 staining of K562 cell line. Untreated K562 cells were without apoptosis, which have 83.1% red fluorescing J-aggregates and 15.6% green fluorescing monomers (FIG. 8Ba). The increase in green fluorescing monomers 47% shown in the lower part indicate apoptotic cells due to the treatment with 140 µg/ml PC:SA MLV liposome for 2 hours (FIG. 8Bb). The results revealed that untreated cells were without apoptosis, which have more red fluorescing J-aggregates and less green fluorescing monomers. The increase in green fluorescing monomers shown in the lower part indicate apoptotic cells due to the treatment with PC:SA liposome and PC:SA-CPT respectively.

Example 9

DNA Cell Cycle Analysis

Treatment of tumor cells with cytotoxic agents usually results in the breakdown of the cell cycle machinery, the cells subsequently entering into programmed cell death or apoptosis. Cell growth arrest occurs in response to cell damage due to oxidative stress or DNA damaging chemicals. These stresses induce the tumor suppressor protein p53, which arrests the cell cycle in $G_1$ or $G_2/M$. P53 is a transcription factor that represses expression of certain cyclins and Cdks, and directly induces the Cdk inhibitor p21. Cell growth arrest allows cells to repair damages. Sub-$G_0/G_1$ accumulation is usually considered as an apoptotic death profile. Cell cycle analysis was done to observe the effect of PC:SA liposome on the cell cycle machinery of the different cells and also to see the mode of action of the liposome. The cationic liposome caused anticancer effect by either apoptosis or via cell cycle arrest in different cell lines. This experiment has a far reaching implication as the mode of action can give us a clear idea of the cell cycle proteins that are involved in the process and can be targeted for future clinical intervention.

Figure 9A:
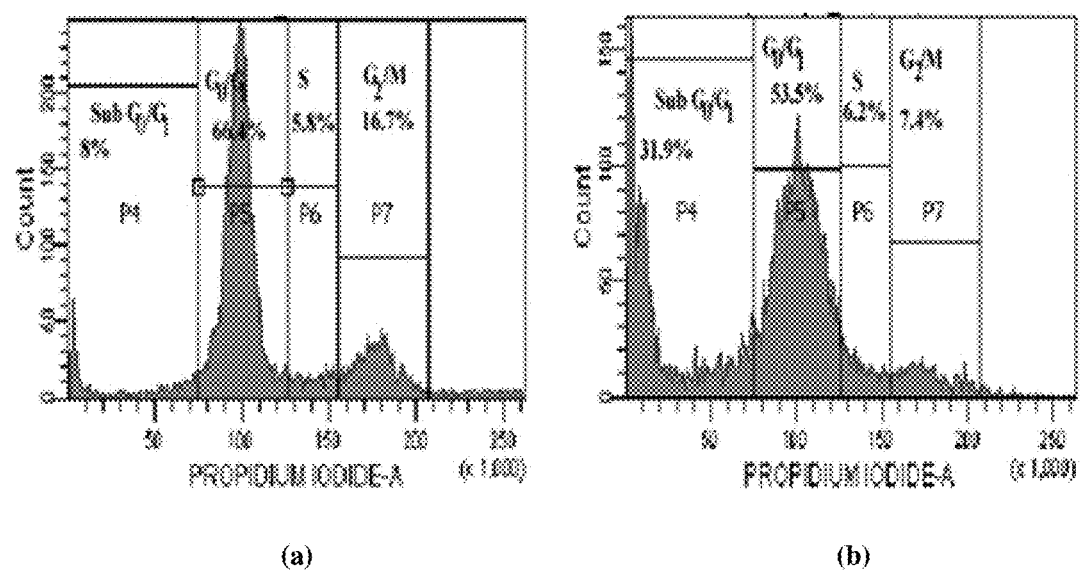
Figure 9E:
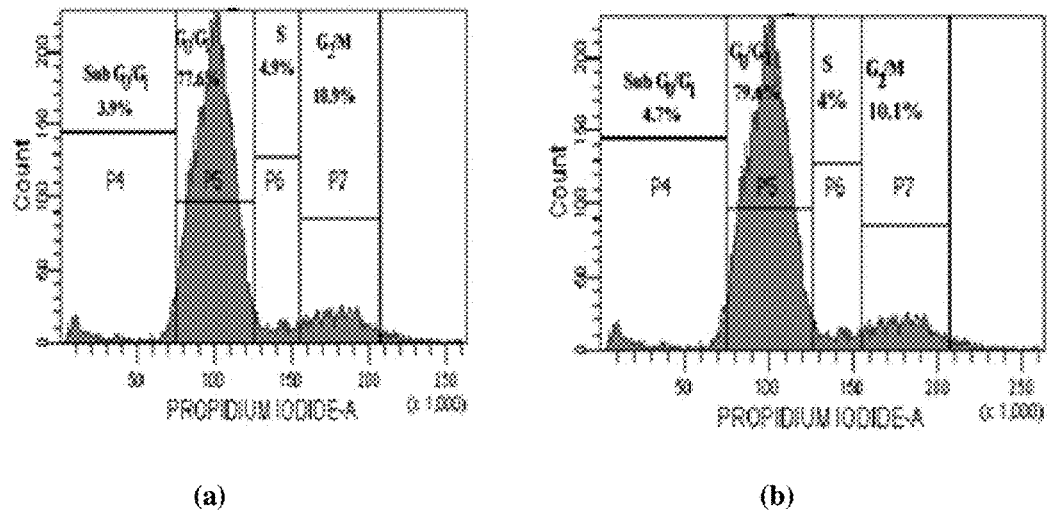
Figure 9F:
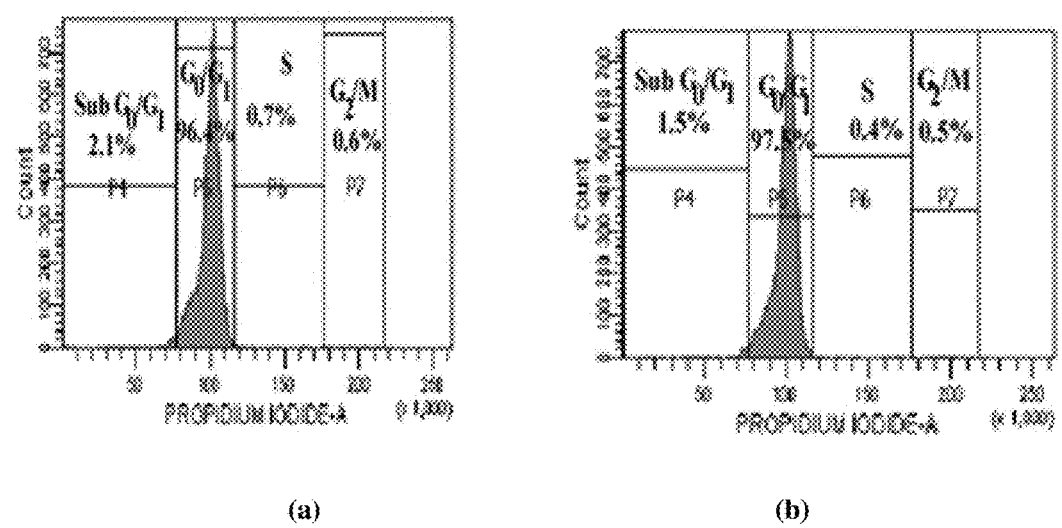

Cell cycle analysis was performed. Briefly, untreated or PC:SA-treated cells were washed twice in PBS. Pelleted cells were fixed in 70% cold ethanol and incubated overnight at −20° C. After two washes in PBS, the cells were resuspended in 0.5 ml of PI (10 µg/ml in PBS) containing RNaseA (248 U/ml), and the mixture was incubated for 20 min in the dark at room temperature. The fluorescence intensity of PI was then analysed with a FACS Calibur flow cytometry and Cell Quest software (28). $G_0/G_1$ proportion in untreated B16F10, K562, U937, RAW 264.7 and PBMC, is 66.4%, 52.11%, 38.2%, 77.6% and 96.4% respectively. Sub $G_0/G_1$ represents 8%, 5.5%, 3.34%, 3.9% and 2.1% of cells respectively (FIGS. 9Aa, 9Ba, 9Ca, 9Ea and 9Fa). Following 2 h of 140 µg/ml of PC:SA (MLV) liposome with respect to PC exposure on B16F10, K562 and U937 the $G_0/G_1$ represents 53.5%, 30.8% and 30.6% of cells respectively while the sub $G_0/G_1$ increased up to 31.9%, 37.69% and 6.13% respectively showing appearance of apoptotic nuclei (Sub $G_0/G_1$ peak in DNA cell cycle analysis) (FIGS. 9Ab, 9Bb and 9Cb). After 4 h treatment of U937 cells sub $G_0/G$, further increased to 12.72% (FIG. 9Cc). $G_2/M$ represents 13.63% of cells in untreated U937 cell line (FIG. 9Ca). Following 2 h and 4 h of 140 µg/ml of PC:SA (MLV) liposome exposure, the $G_2/VI$ increases up to 14.41% and 15.85% respectively. (FIGS. 9Cb and 9Cc). In untreated MOLT4 cell line, $G_0/G_1$ proportion is 69.8% and G2/M represents 13.8% of cells (FIG. 9 Da). Following 4 h of 140 µg/ml of PC:SA liposome (MLV) exposure, the $G_0/G$, represents 62.2% of cells while the $G_2/M$ increases up to 21.3%. (FIG. 9Db). Thus 140 µg/ml of PC:SA liposome exposure leads to $G_2/M$ arrest in U937 and MOLT4 cell lines. When non-cancerous cells RAW 264.7 and PBMC cells were treated with 140 µg/ml of PC:SA liposome (MLV) no significant increase in either sub $G_0/G$, or $G_2M$ was observed. Only 4.7% of the RAW 264.7 cells were in sub $G_0/G_1$ phase after treatment with 140 µg/ml of PC:SA liposome for 2 h (FIG. 9Eb). Similarly very negligible percentage of PBMC cells i.e. 2.1% were in sub $G_0/G$, phase after treatment with 140 µg/ml of PC:SA liposome for 4 h (FIG. 9Fb).

In the above cell cycle analysis it is evident that PC:SA at 140 µg/ml of treatment arrested $G_2/M$ phase in MOLT 4 in 4 h of treatment. In U937 PC:SA at 140 µg/ml of treatment for 2 and 4 h arrested $G_2/M$ phase as well as appearance of apoptotic nuclei as evident by sub $G_0/G_1$ peak. Whereas in K562 cells treatment of PC:SA causes apoptosis within 2 and 4 h of treatment as evident by sub $G_0/G_1$ peak. PC:SA treatment also causes appreciable apoptosis in B16F10 cells as evident by sub $G_0/G_1$ peak. It showed only marginal effect on RAW264.7 and PBMC of healthy donor.

Example 10: Measurement of Reactive Oxygen Species (Ros) Level

Reactive oxygen species (ROS) are long known as general mediators of apoptosis. The dye H2DCFDA which is used for ROS estimation is freely permeable across cell membranes and is incorporated into hydrophobic regions of the cell. The acetate moiety is cleaved by cellular esterases, leaving impermeant, nonfluorescent. 2',T-dichlorodihydrofluorescein (H2DCF). The H2DCF is oxidized by reactive oxygen species to dichlorofluorescein (DCF), which emits fluorescence at 530 nm in response to 488 nm excitation.

K562, U937 and MOLT4 cell lines at 5×10$^5$ cells/ml were treated with 40 µg/ml and 140 µg/ml of doses of PC:SA MLV liposome with respect to PC for 4 h and B16F10 and RAW 264.7 were treated with same doses for 2 h. Additionally K562 cells were treated with different concentrations of PC:SA liposome for 2 h. For each cell line an untreated control was kept. Cells were centrifuged at 4000 rpm for 3 min to remove the culture media and were washed twice in 0.02 M PBS by centrifugation at 4000 rpm for 3 min. The pellet was then suspended in 0.02 M PBS and was loaded with 10 µM Carboxy-DCFDA followed by incubation for 30 min at 31° C. in waterbath. Carboxy-DCFDA is a cell-permeable indicator for ROS that is non fluorescent until the acetate groups are removed by intracellular esterases and oxidation occurs within the cell. When oxidized by various active oxygen species, it is irreversibly converted to the fluorescent form, DCF. Fluorescence was measured through a spectrofluorimeter (LS 3B; PerkinElmer, USA) using 499 nm as excitation and 520 nm as emission wavelengths. Data obtained as fluorescence intensity unit. The data were normalized to normal values, which was expressed as 100% (35). Human PBMC of healthy donor after treatment with 40 µg/ml and 140 µg/ml of PC:SA (MLV) liposome for 4 h showed no increase in ROS level. U937, K562 and MOLT4 cell lines showed increase in ROS level up to 200%, 300% and 200% respectively after treatment with 40 µg/ml of PC:SA (MLV) liposome for 4 h where as ROS level increased up to 400%, 405% and 300% respectively after treatment with 140 µg/ml of PC:SA (MLV) liposome for 4 h. No change in ROS level was observed in RAW 264.7 cell line treated with 40 µg/ml and 140 µg/ml of PC:SA (MLV) liposome. In B16F10 cell line treatment with 40 µg/ml of PC:SA (MLV) liposome for 2 h showed an increase in ROS level up to 300% and treatment with 140 µg/ml of PC:SA (MLV) liposome for 2 h showed an increase in ROS level up to 500% (FIG. 10A).

Different doses of PC:SA liposome (20-140 µg/ml) treatment for 2 h led to increase of intracellular ROS formation compared with untreated cells in K562 cell line (FIG. 10B). The results revealed that K562, MOLT4, U937 and B16F10, after treatment with PC-SA liposome led to increase of intracellular ROS formation compared with control cells which was measured by conversion of H$_2$DCFDA to 2,7-dichloroflurescein. RAW 264.7 and PBMCs after treatment with PC:SA did not show increase in ROS.

Example 11: Detection of Caspase Dependent and Independent Mode of Cell Death

Treatment with caspase inhibitor Z-VAD-fmk reduced the ROS generation and also inhibited PC:SA liposome-induced apoptotic cell death, indicating the role of mitochondrial ROS in PC:SA-induced cell death. K562 cells were preincubated for 2 h with pancaspase inhibitor Z-VAD-FMK (10 µM), washed in PBS, and subsequently incubated with different doses of PC:SA liposome (20-140 µg/ml) with respect to PC. Viability of the cells was checked by MTT assay as described above (36). The results revealed that Z-VAD-fmk treatment reversed the killing effect of PC-SA liposome on K562 cell as indicated by MTT assay. In Z-VAD-fmk treated cells the percent of viable cells increased from 4% to 29%, 37% to 68%, 49% to 77% and 57% to 75% at 140, 120, 100 and 80 µg/ml doses of PC:SA liposome respectively after 2 h of treatment. Thus indicating caspase dependent mode of cell death (FIG. 11).

Example 12: Detection of Morphological Changes in U937 Cells on Treatment with PC:SA Liposome by Transmission Electron Microscopy (TEM)

Surface morphology of PC:SA liposome-treated cancer cells was studied by transmission electron microscopy (TEM). Briefly, cells were fixed in 3% glutaraldehyde in PBS, post-fixed with 1% OsO4 for 16-20 h, gradually dehydrated in ethanol and finally embedded in SPURRT resin. Thin cut sections were stained with uranyl-acetate and lead acetate and were observed in a JEOL-100CX electron microscope (34). Electron microscopic study of untreated and treated (40 µg/ml and 140 µg/ml of PC:SA liposome with respect to PC) U937 cells revealed a stark difference in the morphology of the cells. FIG. 12a shows that TEM representation of control untreated cells with round shape and intact membrane. FIG. 12b shows that treatment of U937 cells with PC:SA liposome (40 µg/ml) causes the morphology of the cells to change. Disruption of membrane integrity was seen. FIG. 12c shows that after treatment with the highest dose of PC:SA liposome (140 µg/ml), the membrane of some cells have disintegrated and large vacuoles are formed as well as depletion of electron-dense cytoplasmic material indicating that the cell death is in process. Hence, TEM observations indicate that membrane disruption occurs on interaction of PC:SA with PS on the cell membrane of cancer cells leading to killing of the cell.

Example 13: Study of Mechanism of Anti-Cancer Effect of PC:SA

Western blot analysis was done to elucidate the molecular mechanism of PC:SA-mediated effect. The experiment elucidates the different kinases that might be involved in the PC:SA-mediated killing effect of cancer cells. The result of immunoblot analysis has a far-reaching impact as this shall clearly demonstrate the pathway involved in the process. Activation of ERK stimulates downstream signaling cascades and also modifies transcription causing apoptotic changes. Caspase 9 when cleaved gets activated and forms part of the apoptosome complex and activates caspase 3 downstream which is also cleaved by PC:SA treatment. Involvement and activation of ERK indicates MAPK mediated apoptotic pathway. Involvement of p21 and and other cell cycle proteins indicates the hindrance of cell cycle pathway as a probable mechanism for PC:SA mediated anticancer effect in some cell types. PC:SA mediated killing activates Bid which is an abundant pro-apoptotic protein of Bcl-2 family and is crucial for death receptor-mediated apoptosis.

The phosphatidylinositol-3-kinase (PI3K)/serine/threonine kinase (Akt) signaling pathway is essential to the survival and proliferation of human cells, and constitutive activation of this pathway is thought to play a critical role in the progression of human hematologic malignancies. Inhibitors of this pathway have been shown to induce apoptosis in isolated leukemia, lymphoma, and myeloma cells. Downregulation of p-PI3K indicates apoptotic mode of cell death in PC:SA treated cells.

B16F10 and RAW 264.7 cell lines were treated with PC:SA MLV liposome at 140 µg/ml with respect to PC for 2 h. U937 cells were treated with graded concentrations (20-140 µg/ml) of PC:SA liposome with respect to PC for 2 h. Untreated cell lines served as controls. The respective cells were kept in RIPA buffer and PMSF overnight at −80° C. Next day the suspension was centrifuged at 8000 rpm for 10 min and the supernatant containing the extracted proteins were collected. The protein content of the extracts was estimated by Lowry's method. Equal amount of proteins (100 μg each) were taken and heated with 0.1 volumes β-mercaptoethanol (4× loading buffer with loading dye) for 5-8 min at 80-90° C. and subjected to electrophoresis on 10% SDS-PAGE. The proteins were electrophoretically transferred on to nitrocellulose membranes. The membranes were blocked with 5% BSA and subsequently washed 3 times with TBST. The membranes were reacted with anti-ERK, anti-phospho-ERK, anti-Caspase 8, anti-cleaved Caspase 9, anti-p21, anti-p38, anti-phospho-p38, anti-Bid, anti-pPI3K and anti-β-Actin primary antibodies at 1/1000 dilution each and kept at 4° C. under constant shaking condition overnight. Next day they were brought back to room temperature and then washed thrice with TBST. The blots were developed using respective HRP coupled secondary antibodies at 1/1000 dilution and kept at 37° C. for 2 h. The blots were then thoroughly washed 4 times with TBST. Bands were visualized using chemiluminescent substrate, Luminol (Super signal West Pico Chemilluminent Substrate). In the chemiluminescence reaction horseradish peroxidase catalyzes the oxidation of luminol in presence of hydrogen peroxide into a reagent (3-aminophthalate) which emits light when it decays. This light was quickly captured in hardcopy on X-Ray films (37).

For estimation of protein by Lowry's method: Standard solution (known conc: 20 μg/20 μl) was made by adding 20 μl BSA+80 μl 0.1 N NaOH+500 μl alkaline $CuSO_4$ solution+ 50 μl Folin's Ciocalteu reagent. Sample solution was made by adding 10 μl sample (whose protein content is to be measured)+90 μl of 0.1 NaOH+500 μl alkaline $CuSO_4$ solution+50 μl Folins Ciocalteu reagent. Blank (buffer for autozero) was made by adding 100 μl 0.1N NaOH+500 μl alkaline $CuSO_4$ solution+Folin's Ciocalteu reagent. The samples were vortexed and kept in dark for 30 min. Optical density (OD) was measured using a spectrophotometer (Pharma Spec UV-1700), at 750 nm. Protein content of the samples were calculated with respect to standard (38).

Stripping for reprobing western blots: The stripping buffer (20 ml SDS 10%, 12.5 ml Tris HCl pH 6.8 0.5 M, 67.5 ml ultra pure water and 0.8 ml β-mercaptoethanol) was warmed to 50° C. in a waterbath. The blot was taken in a tight plastic box and immersed in the stripping buffer and was incubate at 50° C. for up to 45 min with some agitation. The buffer was then disposed off and the membrane rinsed thoroughly under running tap water and then in TBST for several times as a interval of 5 mins until the β-mercaptoethanol smell is gone since traces of β-mercaptoethanol will damage the antibodies. The membrane is then ready for the blocking stage and proceeds as per rest of the western blotting procedure (Abcams protocol).

Figure 13A:
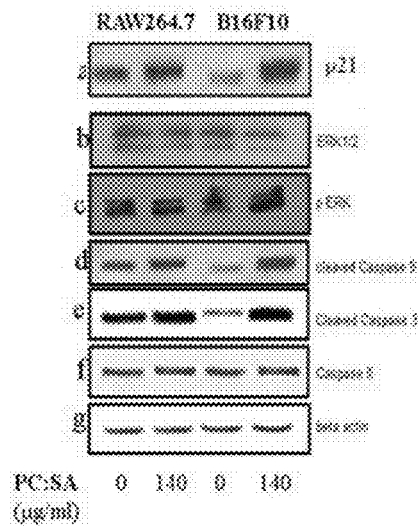
Figure 13B:
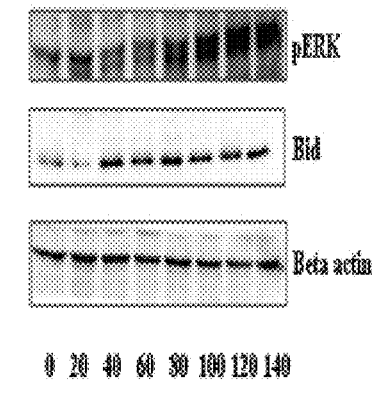

Immunoblot analysis demonstrated that 140 μg/ml of PC:SA treatment with respect to PC for 2 h does not change the expression of ERK (FIG. 13Ab), or Caspase 8 (FIG. 13Af) but causes an appreciable increase in the level of p21 (FIG. 13Aa) phosphorylation of ERK (FIG. 13Ac), cleaved caspase 9 (FIG. 13Ad) and caspase 3 (FIG. 13Ae) in B16F10 cells. RAW 264.7 was used as a control cell line. Beta actin was used as loading control (FIG. 13Ag). The result clearly demonstrates the involvement of ERK activation in PC:SA-mediated anticancer effect. The increase in the level of cleaved caspase 9 and caspase 3 is a clear indication of caspase-mediated apoptotic pathway being involved in PC:SA mediated response. p21 involvement indicates the role of cell cycle machinery being involved in the PC:SA-mediated response. U937 cells treated with different concentrations (20-140 μg/ml) of PC:SA liposome with respect to PC for 2 h results in increased phosphorylation of ERK and activation of pro-apoptotic molecule called Bid (FIG. 13B). The study in FIG. 14 was undertaken to ascertain that 140 μg/ml of PC:SA liposome down-regulates the PI3K/Akt signaling pathway in K562 cell line treated for 90 and 120 min concurrently with induction of apoptotic cell death.

Example 14

Effect of PC:SA Liposome on Ehrlichs Ascites Carcinoma (EAC)

Based on the promising in-vitro results we have initiated studies looking into the effect of PC:SA liposome in-vivo. Ehrlich Ascites Carcinoma (EAC) at $2 \times 10^6$ cells was injected intra-peritoneally into 6 weeks old Swiss Albino mice. After 3 days of EAC injection, the mice were treated intraperitoneally or intravenously with 1.7 g/kg body weight i.e 60 mg of PC:SA or PC:Chol liposomes/mice with respect to PC. The animals were observed for another two weeks and then sacrificed and photographed to study the effect of liposomal treatment. Intraperitoneal fluid was also taken out and the cell counts were done to determine the efficacy of PC:SA treatment (39).

The effect of PC:SA liposome on the body weights of the EAC-bearing mice were examined. On day 14 the body weights of EAC-injected control mice was 39 gm and no significant difference was found in EAC-injected mice treated with PC:Chol liposome (39 gm). In contrast in EAC-injected mice treated with PC:SA liposome (i.v) a significant difference was found in the body weights (29 gm). The effect of PC:SA on the accumulation of ascites fluid was examined on day 14: The volumes of the fluid in the EAC-injected control mice were very large with no difference in EAC-injected mice treated with PC:Chol liposome. In contrast in EAC-injected mice treated with PC:SA liposome the ascites fluid was reduced to one-fourth of the volume in EAC-injected control group. The effect of PC:SA liposome on the number of EAC cells in PC:SA treated and untreated carcinoma-bearing mice was also determined. The number of EAC cells in EAC-bearing control mice was very large. When EAC-injected mice were treated with PC:Chol liposome there was no change in the EAC cell number whereas EAC-injected mice treated with PC:SA liposome showed almost $1/200^{th}$ of the cell number in control mice (FIG. 15 and table 4). The results revealed that a single shot injection of 60 mg of PC:SA (i.p. and i.v.) inhibited the growth of Ehrlichs ascites carcinoma in Swiss albino mice.

TABLE 4

| TREATMENT | WEIGHT OF ANIMAL (gm) N = 3 | NUMBER OF EAC CELLS ($1 \times 10^8$/ml) N = 3 | VOLUME OF PERITONEAL FLUID (ml) N = 3 | VOLUME OF PACKED CELLS (ml) N = 3 |
|---|---|---|---|---|
| CONTROL | 39.67 ± 3.18 | 4 ± 1.3 | 13 ± 0 | 2 ± 0 |
| PC:SA-60 mg (I.P) | 39.67 ± 1.45 | 0.07 ± 0.015 | 3 ± 0.57 | 0.2 ± 0.09 |
| PC:SA-60 mg (I.V) | 29.23 ± 2.25 | 0.02 ± 0.012 | 3 ± 1.014 | 0.07 ± 0.05 |
| PC:Chol-60 mg (I.V) | 40.3 ± 0.89 | 3.2 ± 0.61 | 12.6 ± 0.33 | 1.8 ± 0.15 |

Example 15

Effect of PC:SA and CPT-Entrapped Liposome on Tumor Development in Syngenic Black Mice Protective aspect: As PC:SA and CPT entrapped PC:SA liposomes inhibited cell proliferation in vitro, we first examined its protective effects on tumor cell proliferation in vivo by injecting $2\times10^6$ B16F10 cells pretreated for 2 h with 7 mg/kg body weight i.e 140 µg of PC:SA (respect to PC) alone, and 350 µg/kg body weight i.e 7 µg CPT entrapped in liposomes in C57BL6 mice subcutaneously. The mice were sacrificed after 21 days and tumor growths were observed. Tumor volume in B16F10 cells injected control mice was very large (7.8 cm$^3$) in comparison to mice pre-treated with 140 µg of PC:SA liposome (1.56 cm$^3$) with further reduction in tumor volume to almost negligible levels (0.78 cm$^3$) when pre-treated with 7 µg CPT entrapped liposome (FIG. 16A and table 5).

Therapeutic aspect: Next we examined the therapeutic effects of PC:SA and CPT entrapped in PC:SA liposomes on tumor cell proliferation in C57BL6 mice in vivo. Mice were injected with $2\times10^6$ B16F10 cells on day 0 and then treated on day 2 with 140 µg of PC:SA liposome with respect to PC subcutaneously. In another set of experiment animals were injected with B16F10 cells on day 0 and then treated on day 2 with 7 µg of CPT entrapped in 140 µg of PC:SA liposome. Untreated mice injected with B16F10 cells were kept as control. Mice were sacrificed after 21 days and tumor growths were observed. Tumor volume in control group was larger (31.46 cm$^3$) than in PC:SA treated group (7.7 cm$^3$) and in PC:SA-CPT treated group it was much smaller (2.08 cm$^3$) (FIG. 15B and table 6). We demonstrated that PC:SA liposome itself has anti-tumor activity by inhibiting cell proliferation in in vivo C57BL6 mice and CPT-entrapped PC:SA liposome was more effective than free liposome.

TABLE 5

| Animals Sacrificed | No of animals | Average Body Weight in grams | Tumour dimensions Height | Length | Breadth |
|---|---|---|---|---|---|
| Healthy Control | 2 | 19 | 0 | 0 | 0 |
| Treated Control | 4 | 30 | 2 cm | 2.3 cm | 2.5 cm |
| PC:SA treated | 4 | 27 | 1 cm | 1.2 cm | 1.3 cm |
| CPT-entrapped PC:SA treated | 4 | 21 | 1 mm | 3 mm | 2.6 mm |

TABLE 6

| Animals sacrificed | No of animal | Average body wt in gms | Tumor dimensions Height | Length | Breadth |
|---|---|---|---|---|---|
| Healthy control | 2 | 29 | | | |
| Treated control | 6 | 38 | 2.9 cm ± 0.2 | 3.1 cm ± 0.3 | 3.5 cm ± 0.6 |
| PC:SA treated | 6 | 34 | 1.4 cm ± 0.1 | 2.5 cm ± 0.2 | 2.2 cm ± 0.4 |
| CPT-entrapped PC:SA treated | 6 | 32 | 1 cm ± 0.4 | 1.6 cm ± 0.4 | 1.3 cm ± 0.5 |

Example 16

Effect of PC:SA Liposome on DEN Induced Hepatocarcinoma in Rats

Adult male Swiss Albino rats, each weighing approximately 100-120 g were divided into three groups of three animals each. Rats in group A were kept as normal healthy, these animals were injected with three doses of olive oil (0.5 ml) (i.p) at an interval of 15 days. All rats in the experimental groups were injected with three doses of DEN (i.p) 200 mg/kg body wt in 0.5 ml olive oil at 15 days interval. Group B animals were kept as DEN administered control. Animals in group C were treated with three doses of 800 mg/kg body weight i.e 80 mg (in 0.8 ml) of PC:SA (i.v) from the 7th day of 1$^{st}$ DEN administration at 15 days of interval. At the end of 18 week starting from the 1st day of DEN administration, the final body weight was measured and blood was collected from heart in the rats of each group. Serum aspartate transaminase (AST), alkaline phosphatase (AP) and serum alanine transaminases (ALT) were determined using a standard kit manufactured by Span Diagnostics Ltd. After collection or blood, all rats were dissected and their livers were isolated promptly and washed with cold physiological saline. Final liver weights of all animals were recorded and relative liver weights (RLW) were calculated. A part of the organ was fixed in 10% formaldehyde and processed overnight, and paraffin wax embedded. Sections were stained with hematoxylin and eosin (H&E) for histopathological.

TABLE 7

| Group | Liver Weight (g) | Relative liver weight (RLW) | % increase of RLW |
|---|---|---|---|
| Normal | 6.67 ± 0.77 | 2.56 ± 0.10 | |
| DEN | 7.67 ± 0.61 | 3.39 ± 0.17 | 32.33 |
| DEN + PC:SA | 5.99 ± 0.17 | 3.07 ± 0.19 | 20.16 |

DEN (3 doses of i.p. 200 mg/kg b.wt at 15 day interval) treatment causes an increase in relative liver weight (RLW) in rats. PC:SA (3 doses of i.v. injection of 800 mg/kg body weight i.e 80 mg in 0.8 ml at 15 days interval) liposome prevented increase in RLW of liver in rats significantly in comparison to DEN administered control group (table 7).

Haematoxylin Eosin-stained liver sections of normal rat showed hepatocytes are arranged in cords around hepatic vein forming hepatic lobules. Portal tracts are normal. DEN injected animals show dialated hepatic veins and hepatic micronodules separated by thin fibrous septum. However PC:SA liposome have prevented the liver from developing hepatocarcinoma. Normal looking hepatic vein, portal tracts and hepatocytes are present here but some amount of periportal fibrosis are not prevented (FIG. 17). In the assessment of liver damage by DEN the determination of enzyme levels was largely used. Serum SGPT, SGOT and ALP are the most sensitive markers employed in the diagnosis of hepatic damage because these are cytoplasmic in location and are released in to the circulation of after cellular damage. In this study, an increase in the activities of SGPT, SGOT and ALP in serum evidenced the DEN-induced hepatocellular damage. The reduction of DEN-induced elevated plasma activities of these enzyme levels in animals treated with PC:SA liposome showed their ability to restore the normal functional status of the damaged liver. The results of this study clearly demonstrated that PC:SA lipo-

Example 17

Comparison of In Vitro $EC_{50}$ of PC:SA and Anticancer Drugs on Different Cell Lines $5\times10^5$ cells/ml of murine melanoma cell line B16F10, rat brain astrocytes, colorectal adenocarcinoma SW480 cell line, human colon carcinoma HCT116 cell line, rat brain astrocytes, human neuroblastoma SH5YSY, human hepatocarcinoma HepG2, humancervical carcinoma HeLa, human breast cancer MCF7, adeno gastric carcinoma AGS, colorectal adenocarcinoma SW480 cell line human embryonic kidney HEK, mouse fibroblast NIH3T3 and rat C6 glioma cell lines were seeded in Dulbecco Modified Eagle Medium (DMEM) supplemented with 10% fetal bovine serum, sodium pyruvate, 2 mM L-glutamine, penicillin, and streptomycin in 96 well cell culture plate. $5\times10^5$ cells/ml of murine macrophage cell line RAW 264.7, MOLT-4, MOLT3 cell line (derived from human acute lymphoblastic leukemia), human leukemia cell lines K-562 and human lymphoma cell line U-937, healthy human PBMC, Ehrlichs ascites carcinoma (EAC) were seeded in RPMI 1640 medium supplemented with 10% fetal bovine serum, sodium pyruvate, 2 mM L-glutamine, penicillin, and streptomycin in 96 well tissue culture plate. The cells were treated with PC:SA liposome (20-350 µg/ml with respect to PC) or free DOX (500-1000 µg/ml) and free CAMPTOSAR (irinotecan hydrochloride, which is a semisynthetic derivative of camptothecin) (500-10,000 µg/ml). After 2 h of treatment effects on cell viability were determined by MTT assay. $EC_{50}$ values were determined by nonlinear regression analysis of concentration-response data.

PC-SA liposome selectively killed murine melanoma cell line B16F10, human neuroblastoma cell line SH-SY5Y, colorectal adenocarcinoma SW480 cell line, human colon carcinoma HCT116 cell line, rat C6 glioma, MOLT-3, MOLT4 cell line (derived from human acute lymphoblastic leukemia), human leukemia cell lines K-562, human lymphoma cell line U-937, PBMC of acute promyelocytic leukemia and AML patients, Ehrlichs ascites carcinoma cells (EAC) and adeno gastric carcinoma AGS cell line (half-maximal effective concentration ($EC_{50}$)=65-170 µg/ml for 2 h treatment, respectively) (FIG. 19a). However it showed weaker killing activity against non-cancerous and cancer cell lines including human embryonic kidney HEK, mouse fibroblast NIH3T3, macrophage cell line RAW 264.7, human peripheral blood mononuclear cells (PBMC), human breast cancer MCF7, human liver cancer HepG2, human cervical carcinoma HeLa, and rat brain astrocytes ($EC_{50}$=218-480 µg/ml), with less surface exposed PS (FIG. 19 a) indicating that PC-SA liposomes probably do not kill cells through an off-target mechanism.

Free CAMPTOSAR (irinotecan hydrochloride, which is a semisynthetic derivative of camptothecin) and doxorubicin (DOX) were tested for the effects of these anticancer drugs on seven cancer cell lines B16F10, K562, U937, rat C6 glioma, 0937, EAC, MOLT4 and SW480 cell lines. FIG. 19 b revealed that $EC_{50}$ values of free irinotecan hydrochloride (a semisynthetic derivative of CPT) were in the range of 800-5,000 µg/ml and the $EC_{50}$ values of free DOX was in the range of 500 µg/ml-800 µg/ml. The above example revealed that free liposome PC-SA is itself a very potent anticancer agent. In vitro studies shows that $EC_{50}$ value of free liposome against some of the cancer cell lines is in the range of 65-170 µg/ml whereas the $EC_{50}$ value of free anticancer drugs like doxorubicin and irinotecan hydrochloride (a semisynthetic derivative of camptothecin i.e. its injection formulation) is in the range of 500-5000 µg/ml i.e. almost 8 to 30 times more than that of free liposome when treated for 2 h. The free lipsome is much more potent than free known anti-cancer drugs. The $EC_{50}$ value of free liposome is higher against non-cancer and some of other cancer cell lines which have less PS content. Therefore, PC:SA lipsome is effective against PS containing cancer cells only and not against non-cancerous and less PS containing cancer cells.

FIG. 19: Comparison of the effect of PC:SA liposome and free anticancer drugs on cancer cell lines in vitro.

The viability of all the cell types was measured by inhibition of 3-(4, 5-dimethylthiozol-2-yl)-2, 5-diphenyltetrazolium bromide (MTT) reduction to insoluble formazan by mitochondrial dehydrogenase after 2 h of treatment. The $EC_{50}$ values of free PC:SA liposome (a), free irinotecan hydrochloride (semisynthetic derivative of CPT) and DOX (b) for in vitro killing of cell lines. Error bars denote standard deviation of 3 experiments.

The free liposome PC-SA is itself a very potent anticancer agent. In vitro studies shows that $EC_{50}$ value of free liposome against some of the cancer cell lines is in the range of 60-80 µg/ml whereas the $EC_{50}$ value of free anticancer drugs like doxorubicin and irinotecan hydrochloride (a semisynthetic derivative of camptothecin i.e. its injection formulation) is in the range of 700-5000 µg/ml i.e. almost 10 to 60 times more than that of free liposome when treated for 2 h. The free lipsome is much more potent than free known anti-cancer drugs. The $EC_{50}$ value of free liposome is higher against non-cancer and some of other cancer cell lines which have less PS content (FIG. 19). Therefore, PC-SA lipsome is effective against PS containing cancer cells only and not against non-cancerous and less PS containing cancer cells.

Advantages of the Present Invention

1. PC:SA liposome in its 7:2 molar ratio is non toxic to normal human cells like PBMC, whereas some cancer cells are susceptible to the liposome.
2. The unique mode of selectivity towards PS, of various cancer cells and *Leishmania* parasites indicates that the SA-hearing liposomes might be valuable as delivery system as well as therapy not only against cancers and leishmaniasis but possibly also against other diseases which have elevated surface levels of negatively charged phospholipid, i.e. PS.
3. PC:SA liposome is effective in inducing apoptosis of various cancer cell lines without having appreciable effects on normal human peripheral blood mononuclear cells and this might be valuable as therapy as well as for delivery against cancer cells with apoptotic defects.
4. PC:SA liposome mediates apoptosis of various cancer cell lines by, mitochondrial membrane depolarization, generation of ROS, activation of caspases, ERK and downreguiation of PI3K mediated pathway.
5. PC:SA liposome is an alternate drug delivery system that is being used to enhance the therapeutic efficacy and reduce the toxicity of anticancer agents like camptothecin and doxorubicin. PC:SA liposome entrapped camptothecin and doxorubicin are liposomal formulations of camptothecin and doxorubicin designed to increase efficacy, safety and tolerability while potentially delivering higher doses of camptothecin.

6. SA-bearing liposomal anticancer drugs will help in the treatment of cancer with minimal detrimental side-effects.
7. It will provide a strong rationale for the use of our liposomal cytotoxic therapeutic agents for the treatment of human cancer. 8. It will be of great importance to treatments in which toxic substances are needed to combat disease.

REFERENCES

1. WHO Fact Sheet
2. Hanahan D., Weinberg R. A. (2000) The Hallmarks of Cancer. *Cell.* 100, 57-70.
3. Kim R., Emi M. and Tanabe K, (2006). Cancer Immunosuppression and autoimmune disease: beyond immunosuppressive networks for tumour immunity. *Immunology*, 119, 254-264.
4. Kuby J., Kindt Goldby R. A. and Osborne B. A. *Immunology* W H Freeman & Co (Sd) $6^{th}$ ed Pg. 538-539.
5. Shiratsuchi A. and Nakanishi Y. (1999). Phosphatidylserine-Mediated Phagocytosis of Anticancer Drug-Treated Cells by Macrophages *J. Biochem.* 126, 1101-1106.
6. Mayhew E., Itos M. and Lazo R. (1987). Toxicity of Non-Drug-Containing Liposomes for Cultured Human Cells. *Experimental Cell Research.* 171, 195-202.
7. Graham R. and Barbisin M. Cationic liposome and methods of use. (2013). US 2013/0017248 A1.
8. Beck A. W., Luster T. A., Miller A. F., Holloway S. E., Conner C. R., Barnett C. C., Thorpe. P. E., Fleming J. B. and Brekken R. A. (2006). Combination of a monoclonal anti-phosphatidylserine antibody with gemcitabine strongly inhibits the growth and metastasis of orthotopic pancreatic tumors in mice *Int. J. Cancer.* 118, 2639-2643.
9. Utsugi T., Schroit A. J., Connor J., Bucana C. D., and Fidler I. J. (1991). Elevated Expression of Phosphatidylserine in the Outer Membrane Leaflet of Human Tumor Cells and Recognition by Activated Human Blood Monocytes. *Can. Res.* 51, 3062-3066.
10. Schroder-Borm H., Bakalova R. and Andra J. (2005). The NK-lysin derived peptide NK-2 preferentially kills cancer cells with increased surface levels of negatively charged phosphatidylserine. FEBS Lett. 579, 6128-6134.
11. Kenis H. and Reutelingsperger C. (2009) Targeting Phosphatidylserine in Anti-Cancer Therapy. *Current Pharmaceutical Design.* 15.
12. Ran S., Thorpe E. P., (2011) Uses of antibodies to aminophospholipids for cancer treatment. EP2311490 A2.
13. Fanciullino R. and Ciccolini J. (2009) Liposome-Encapsulated Anticancer Drugs: Still Waiting for the Magic Bullet? *Current Medicinal Chemistry.* 16, 4361-437'3.
14. Basu M. K. (2010) Site Specific Drug Delivery. *J. Inst. Chemists* (India). 82. 65-73.
15. Lewin B. (2007) Cells. Jones and Bartlett publishers. Pg 553-554.
16. Judy B. F., Aliperti L. A. Predina J. D., Levine D., Kapoor V., Thorpe P. E., Albelda S. M. and Singhal S. (2012). Vascular endothelial-targeted therapy combined with cytotoxic chemotherapy induces inflammatory intratumoral infiltrates and inhibits tumor relapses after surgery. Neoplasia 14, 352-359.
17. Kirszberg C., Limaa L. G., Oliveiraa A. D. S., Pickeringb E. G., Barrowcliffeb T. W., Rumjaneka V. M. and Monteiroa R. Q. (2009) Simultaneous tissue factor expression and phosphatidylserine exposure account for the highly procoagulant pattern of melanoma cell lines. *Melanoma Research* 19, 301-308.
18. Fernandes R. S, Kirszberg C., Rumjanek V. M. and Monteiro R. Q. (2006) On the molecular mechanisms for the highly procoagulant pattern of C6 glioma cells. *J Thromb Haemost.* 4, 1546-1552.
19. Freazard F. (1999) Liposomes: from biophysics to the design of peptide vaccines. *Brazilian Journal of Medical and Biological Research* 32, 181-189.
20. Stebelska K., Dubielecka P. M. and Sikorski A. F. (2005) The Effect of PS Content on the Ability of Natural Membranes to Fuse with Positively Charged Liposomes and Lipoplexes. *J. Membrane Biol.* 206, 203-214.
21. Banerjee A, De M and Ali N. (2008) Complete cure of experimental visceral leishmaniasis with amphotericin B in stearylamine-bearing cationic liposomes involves down-regulation of IL-10 and favorable T cell responses. *J Immunol.* 181. 1386-98.
22. Banerjee A., Roychoudhury J., and Ali N. (2007) Stearylamine-bearing cationic liposomes kill *Leishmania* parasites through surface exposed negatively charged phosphatidylserine. *Journal pf Antimicrobial Chemotherapy.* 61, 103-110.
23. S. Bhowmick Mazumdar T, Sinha R and Ali N. (2009) Comparision of liposome based antigen delivery systems for protection against *Leishmania clonovani.* *J. of Controlled Release.* 141, 199-207.
24. Espinosa E. et al. (2003) Classification of anticancer drugs—a new system based on therapeutic targets. *Cancer Treatment Reviews.* 29, 515-523.
25. Hatefi A., Amsden B. (2002) Camptothecin Delivery Methods. *Pharmaceutical Research.* Vol 19, 1389-1390.
26. Saeetern A. M., Flaten G. E., and Brandi M. (2004) A Method to Determine the Incorporation Capacity of Camptothecin in Liposomes. *AAPS PharmSciTech.* 5 (3) Article 40.
27. Burke T. G., Staubus A. E. and Mishra A. K. (1992) Liposomal Stabilization of Camptothecin Lactone Ring. *J. Am. Chem. SOC.* 114, 8318-8319.
28. Hatdara K., Zamir L., Shi Q. W. and Batist G. (2005) The flavonoid Casticin has multiple mechanisms of tumor cytotoxicity action. *Cancer Letters.* 1-11.
29. Morgan M. T., Nakanishi Y., Kroll D. J., et al. (2006) Dendrimer-Encapsulated Camptothecins: Increased Solubility, Cellular Uptake, and Cellular Retention Affords Enhanced Anticancer Activity In vitro. *Cancer Res.* 66, 11913-11921.
30. Mondal S., Bhattacharya P., Rahaman M., Ali N. and Goswami R. P. (2010) A curative immune profile one week after treatment of Indian kala-azar patients predicts success with a short-course liposomal amphotericin B therapy. *PLoS Negl Trop Dis.* 4(7):e764.
31. Hung S. Y., Liou H. C., Kang K. H., Wu R. M., Wen C. C., and Fu W. M. (2008) Overexpression of Herne Oxygenase-1 Protects Dopaminergic Neurons against 1-Methyl-Phenylpyridinium-Induced Neurotoxicity. *Mol Pharmacol.* 74, 1564-1575.
32. Bandyopadhyay G., Biswas T., Roy K. C., Mandal S, Mandal C., Bikas C. Pal B. C., Bhattacharya S., Rakshit S, Bhattacharya D. K., Chaudhuri U., Konar A., and Bandyopadhyay S. (2004) Chlorogenic acid inhibits Bcr-Abl tyrosine kinase and triggers p38 mitogen-activated protein kinase-dependent apoptosis in chronic myelogenous leukemic cells. *Blood.* 104, 2514-2522.
33. Sen N., Das B. B., Ganguly A., Mukherjee T., Tripathi G., Bandyopadhyay S., Rakshit S., Sen T. and Majumder H. K. (2004) Camptothecin induced mitochondrial dysfunction leading to programmed cell death in unicellular hemoflagellate *Leishmania donovani*. *Cell Death Differ.* 11, 924-936.

34. Tu S. P., Zhong J., Tan J I. H., Jiang X. H., Qiao M. M, Wu Y. X., and Jiang S. H. (2000) Induction of apoptosis by arsenic trioxide and hydroxy camptothecin in gastric cancer cells in vitro *World J Gastroentero.* 6, 532-539.

35. Dalvit G. C., Cetica P. D., Pintos L. N. and Beconi M. T. (2005). Reactive oxygen species in bovine embryo in vitro production. *Biocell.* 29, 209-212.

36. Ilangovan R., Marshall W. L., Hua Y., and Zhou J. (2003). Inhibition of Apoptosis by Z-VAD-fmk in SMN-depleted S2 Cells. *The Journal of Biological Chemistry* 278, 30993-30999.

37. Idris A. I. (2012). Analysis of Signalling Pathways by Western Blotting and Immunoprecipitation. *Methods in Molecular Biology* 816, 223-232.

38. Lowry J. H., Rosebrough N. J., Farr A. L., and Randall R. J. (1951). Protein measurement with the Folin phenol reagent. *J Biol Chem* 193, 265-275.

39. Ahmed H., Chaterjee B. P., and Debnath A. K. (1988). Interaction and in vivo growth inhibition of Ehrlich ascites tumor cells by jacalin. *J biosci.* 13, 419-424.

40. Fujimura T., Nakagawa S., Ohtani T., Ito Y., and Aiba S., (2006). Inhibitory effect of the polyinosinic-polycytidylic acid/cationic liposome on the progression of murine B16F10 melanoma. *Eur. J. Immunol.* 36, 3371-3380.

41. Ghosh D. Choudhury S. T., Ghosh S., Mandal A. K., Sarkar S., Ghosh A., Saha K. D., and Das N. (2012). Nanocapsulated curcumin: Oral chemopreventive formulation against diethylnitrosamine induced hepatocellular carcinoma in rat. *Chemico-Biological Interactions.* 195, 206-214.

42. Chen Y. Q., Min C., Sang M., Han Y., Ma X., Xue X. Q., Zhang S. Q. (2010). A cationic amphiphilic peptide ABP-CM4 exhibits selective cytotoxicity against leukemia cells. *Peptides.* 31, 1504-1510.

43. Drullion C., Tregoat C., Lagarde V., Tan S., Gioia R., Priault M., Djavaheri-Mergny M., Brisson A., Auberger P., Mahon F-X. and Pasquet. J-M., (2012). Apoptosis and autophagy have opposite roles on imatinib-induced K562 leukemia cell senescence. *Cell Death Dis.* 3, e373.

44. Ozaslan M., Karagoz I. D., Kilic I. H. and Guldur M. E. (2011). Ehrlich ascites carcinoma *African Journal of Biotechnology.* 10, 2375-2378.

45. Miller A., Sullivan J. F. and Katz J. H. (1963). Sialic Acid Content of the Erythrocyte and of an Ascites Tumor Cell of the Mouse. *Cancer Res.* 23, 485-490.

46. Magda I. Y., Maghraby H., Youssef E. A. and El-Sayed M. M. (2012). Expression of Ki 67 in hepatocellular carcinoma induced by diethylnitrosamine in mice and its correlation with histopathological alterations. *Journal of Applied Pharmaceutical Science.* 02, 52-59.

47. Riedl S., Rinner B., Asslaber M., Schaider H., Walzer S., Novak A., Lohner K., Zweytick D. (2011). In search of a novel target—Phosphatidylserine exposed by non-apoptotic tumor cells and metastases of malignancies with poor treatment efficacy. *Biochimica el Biophysica Acta.* 1808, 2638-2645.

48. Nie Y., Ji L., Ding H., Xie L., Li L., He B., Wu Y., Gu Z. (2012). Cholesterol derivatives based charged liposomes for doxorubicin delivery: preparation, in vitro and in vivo characterization. *Theranostics.* 11, 1092-1103.

49. Thorna C. F., Oshiroa C., Marshe S., Hernandez-Boussardb T., McLeodd H., Kleina T. E., and Altmana R. B. (2011). Doxorubicin pathways: pharmacodynamics and adverse effects. *Pharmacogenet Genomics.* 21, 440-446.

We claim:

1. A synergistic liposomal formulation for the treatment of cancer, wherein said synergistic liposomal formulation consists of drug-free phosphatidylcholine (PC) and stearylamine (SA) liposomes, and camptothecin (CPT), doxorubicin (DOX), or combinations thereof, and wherein phosphatidylcholine, stearylamine, and camptothecin w/w molar ratio in said synergistic liposomal formulation is 7(PC):2(SA):0.7 (CPT) or wherein phosphatidylcholine, stearylamine, and doxorubicin w/w molar ratio in said synergistic liposomal formulation is 7(PC):2(SA):0.5(DOX).

2. The synergistic liposomal formulation as claimed in claim 1, wherein, said synergistic liposomal formulation is prepared in a form selected from the group consisting of dehydration-rehydration vesicles (DRV), reverse phase evaporation vesicle (REV), and multilamellar vesicles (MLV).

3. The synergistic liposomal formulation as claimed in claim 1, wherein said synergistic liposomal formulation is used for the treatment of murine melanoma, rat glioma, colorectal adenocarcinoma, human colon carcinoma, chronic myelogenous leukemia, acute lymphoblastic leukemia, and ascites carcinoma in vitro.

4. The synergistic liposomal formulation as claimed in claim 1, wherein the dose of said synergistic liposomal formulation is used at 20-140 μg/ml with respect to PC.

5. A drug-free liposomal formulation for use in the treatment of cancer, wherein said liposomal formulation comprises of phosphatidylcholine (PC) and stearylamine (SA) in a molar ratio of 7:2.

6. The liposomal formulation as claimed in claim 5, wherein EC50 value of said liposomal formulation against cancer cell lines is in the range of 60-80 μg/ml.

7. The liposomal formulation as claimed in claim 5, wherein said liposomal formulation for intravenous administration is 800 mg/Kg body weight.

8. The liposomal formulation as claimed in claim 5, wherein said liposomal formulation for intravenous or intraperitoneal administration is 1.7 g/Kg body weight.

9. The liposomal formulation as claimed in claim 5, said liposomal formulation for subcutaneous administration is 7 mg/Kg body weight with respect to PC.

10. The synergistic liposomal formulation as claimed in claim 1, wherein for subcutaneous administration the anticancer drug CPT is administered at 350 μg/Kg body weight entrapped in 7 mg/Kg body weight of PC-SA.

11. A synergistic formulation consisting of camptothecin (CPT), doxorubicin (DOX), or combinations thereof, and liposomes consisting of phosphatidylcholine (PC) and stearylamine (SA), wherein phosphatidylcholine, stearylamine, and camptothecin w/w molar ratio in said synergistic formulation is 7(PC):2(SA):0.7(CPT) or wherein phosphatidylcholine, stearylamine, and doxorubicin w/w molar ratio in said synergistic formulation is 7(PC):2(SA):0.5(DOX).

12. The liposomal formulation as claimed in claim 5 which consists of phosphatidylcholine (PC) and stearylamine (SA).

\* \* \* \* \*